US012620764B2

(12) United States Patent
Khachaturov et al.

(10) Patent No.: US 12,620,764 B2
(45) Date of Patent: May 5, 2026

(54) METHOD AND SYSTEM FOR ESTIMATING DISTANCE BETWEEN A FIBER END AND A TARGET

(71) Applicant: LUMENIS LTD, Yokneam (IL)

(72) Inventors: Arkady Khachaturov, Haifa (IL);
Vitaly Rondel, Hadera (IL)

(73) Assignee: Lumenis Ltd., Yokneam Ilit (IL)

( * ) Notice: Subject to any disclaimer, the term of this patent is extended or adjusted under 35 U.S.C. 154(b) by 1166 days.

(21) Appl. No.: 17/535,172

(22) Filed: Nov. 24, 2021

(65) Prior Publication Data

US 2022/0160435 A1      May 26, 2022

Related U.S. Application Data

(60) Provisional application No. 63/252,830, filed on Oct. 6, 2021, provisional application No. 63/118,857, filed
(Continued)

(51) Int. Cl.
*H01S 3/067* (2006.01)
*A61B 18/26* (2006.01)
(Continued)

(52) U.S. Cl.
CPC .......... *H01S 3/06725* (2013.01); *A61B 18/26* (2013.01); *A61B 34/20* (2016.02); *H01S 3/10038* (2013.01); *A61B 2034/2055* (2016.02)

(58) Field of Classification Search
CPC ...... G01S 7/4802; G01S 17/08; G01S 7/4812; G01S 7/483; G01S 7/484; G01S 7/4911;
(Continued)

(56) References Cited

U.S. PATENT DOCUMENTS 6,212,310 B1 * 4/2001 Waarts ................. H04B 10/291
385/127
7,831,298 B1 11/2010 Wang et al.
(Continued)

FOREIGN PATENT DOCUMENTS

DE       202016103544 U1 * 8/2017
JP       2011529189 A     12/2011
WO       2008024101 A1    2/2008

OTHER PUBLICATIONS

Nowak et al. "Fast optoelectronic sensor of water concentration", Optica Applicata, vol. XLVI, No. 4, 2016, pp. 607-618 (Year: 2016).*
(Continued)

*Primary Examiner* — Eric L Bolda
(74) *Attorney, Agent, or Firm* — Seager, Tufte & Wickhem, LLP

(57) ABSTRACT

The present disclosure is related to field of Fiber Feedback (FFB) technology, and provides a method and system for estimating the distance between a fiber end and a target. The method includes illuminating, by a Light Emitting, Transmitting and Detecting (LETD) system, the target with laser light of different wavelengths having low and high water absorption coefficients, using different laser light sources, as well as receiving a returned signal corresponding to the incident laser light of different wavelengths, and detecting the returned signal to measure intensity values of the returned signal of a specific wavelength. Using the measured intensity values, a processing unit may estimate distance between the fiber and the target. The present disclosure enables accurate estimation of distance between a fiber end and the target. The present disclosure also provides a robust distance estimation technique which is compatible with different types of targets.

14 Claims, 15 Drawing Sheets

Related U.S. Application Data on Nov. 27, 2020, provisional application No. 63/118,117, filed on Nov. 25, 2020.

(51) Int. Cl.

| | | |
|---|---|---|
| *A61B 34/20* | (2016.01) | |
| *H01S 3/10* | (2006.01) | |

(58) Field of Classification Search
CPC .... G01S 7/4912; G01S 7/499; H01S 3/10038; A61B 34/20; A61B 18/26
See application file for complete search history.

(56) References Cited

U.S. PATENT DOCUMENTS

| | | | |
|---|---|---|---|
| 10,901,074 B1 * | 1/2021 | Pan | G01S 17/89 |
| 2001/0027316 A1 | 10/2001 | Gregory | |
| 2008/0058629 A1 * | 3/2008 | Seibel | A61B 1/07 |
| | | | 600/368 |
| 2010/0019170 A1 | 1/2010 | Hart et al. | |
| 2013/0123769 A1 | 5/2013 | Khatchaturov et al. | |
| 2020/0150251 A1 * | 5/2020 | Crouch | G01S 7/4814 |
| 2020/0249355 A1 * | 8/2020 | Keyser | G01S 17/894 |
| 2024/0192325 A1 * | 6/2024 | Buchter | G01S 7/484 |

OTHER PUBLICATIONS

International Search Report and Written Opinion dated Feb. 23, 2022 for International Application No. PCT/IB2021/060945.

* cited by examiner

111

CUT ANGLE
8 DEG

CUT ANGLE
8 DEG

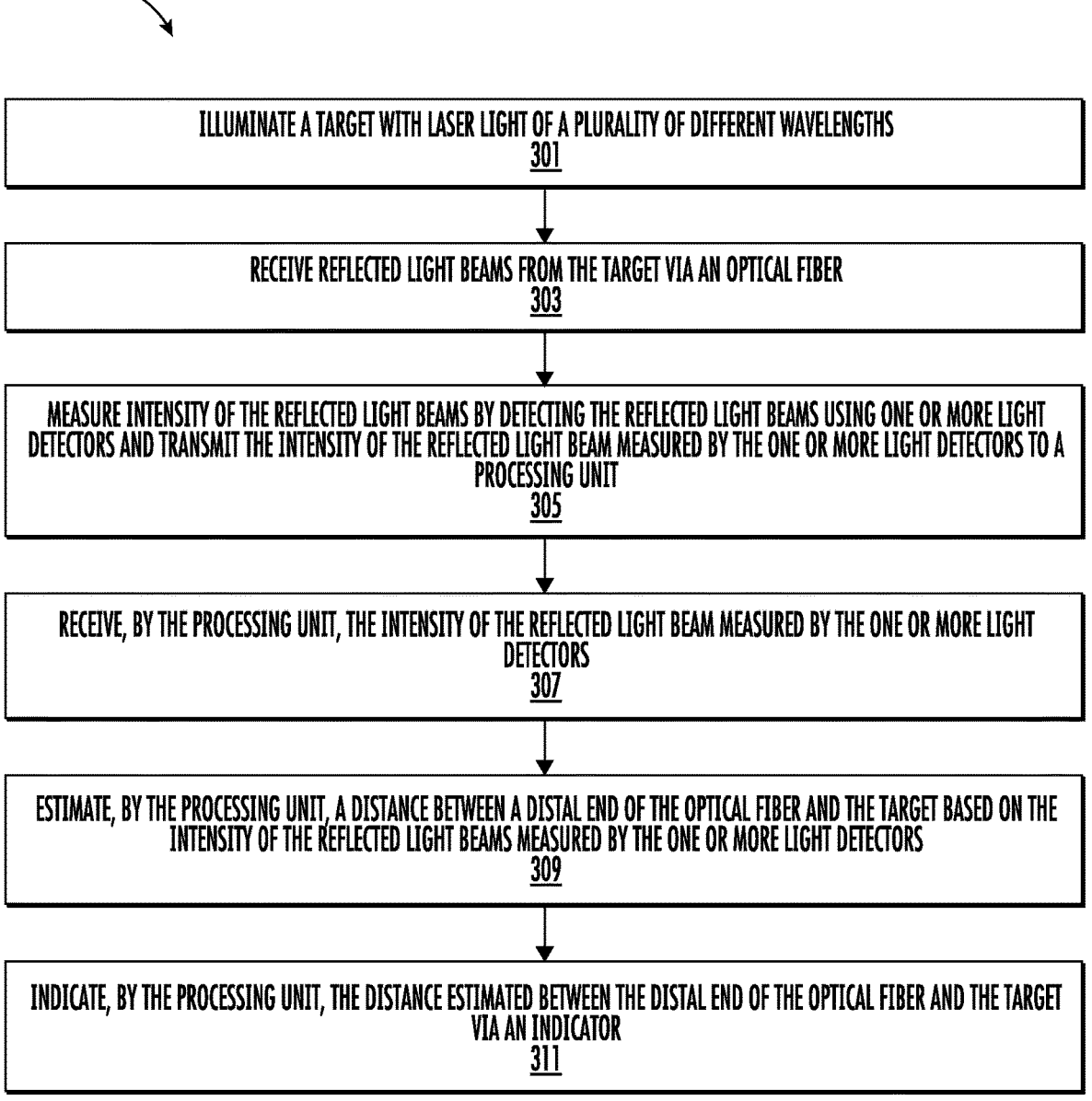

300

ILLUMINATE A TARGET WITH LASER LIGHT OF A PLURALITY OF DIFFERENT WAVELENGTHS
301

RECEIVE REFLECTED LIGHT BEAMS FROM THE TARGET VIA AN OPTICAL FIBER
303

MEASURE INTENSITY OF THE REFLECTED LIGHT BEAMS BY DETECTING THE REFLECTED LIGHT BEAMS USING ONE OR MORE LIGHT DETECTORS AND TRANSMIT THE INTENSITY OF THE REFLECTED LIGHT BEAM MEASURED BY THE ONE OR MORE LIGHT DETECTORS TO A PROCESSING UNIT
305

RECEIVE, BY THE PROCESSING UNIT, THE INTENSITY OF THE REFLECTED LIGHT BEAM MEASURED BY THE ONE OR MORE LIGHT DETECTORS
307

ESTIMATE, BY THE PROCESSING UNIT, A DISTANCE BETWEEN A DISTAL END OF THE OPTICAL FIBER AND THE TARGET BASED ON THE INTENSITY OF THE REFLECTED LIGHT BEAMS MEASURED BY THE ONE OR MORE LIGHT DETECTORS
309

INDICATE, BY THE PROCESSING UNIT, THE DISTANCE ESTIMATED BETWEEN THE DISTAL END OF THE OPTICAL FIBER AND THE TARGET VIA AN INDICATOR
311

FIG. 3A

350

DETERMINE A FIRST INTENSITY VALUE BASED ON FIRST REFLECTED LASER LIGHT CORRESPONDING TO LASER LIGHT OF A FIRST WAVELENGTH WHEREIN THE LASER LIGHT OF THE FIRST WAVELENGTH EXITS A DISTAL END OF AN OPTICAL FIBER AND THE FIRST REFLECTED LASER LIGHT IS REFLECTED BY A TARGET AND ENTERS THE DISTAL END OF THE OPTICAL FIBER
351

DETERMINE A SECOND INTENSITY VALUE BASED ON SECOND REFLETED LASER LIGHT CORRESPONDING TO LASER LIGHT OF A SECOND WAVELENGTH, WHEREIN THE LASER LIGHT OF THE SECOND WAVELENGTH EXITS THE DISTAL END OF THE OPTICAL FIBER AND THE SECOND REFLECTED LASER LIGHT IS REFLECTED BY THE TARGET AND ENTERS THE DISTAL END OF THE OPTICAL FIBER
353

COMPUTE A RATIO OF THE FIRST INTENSITY VALUE AND THE SECOND INTENSITY VALUE
355

ESTIMATE A DISTANCE BETWEEN THE DISTAL END OF THE OPTICAL FIBER AND THE TARGET BASED ON THE RATIO OF THE FIRST INTENSITY VALUE AND THE SECOND INTENSITY VALUE
357

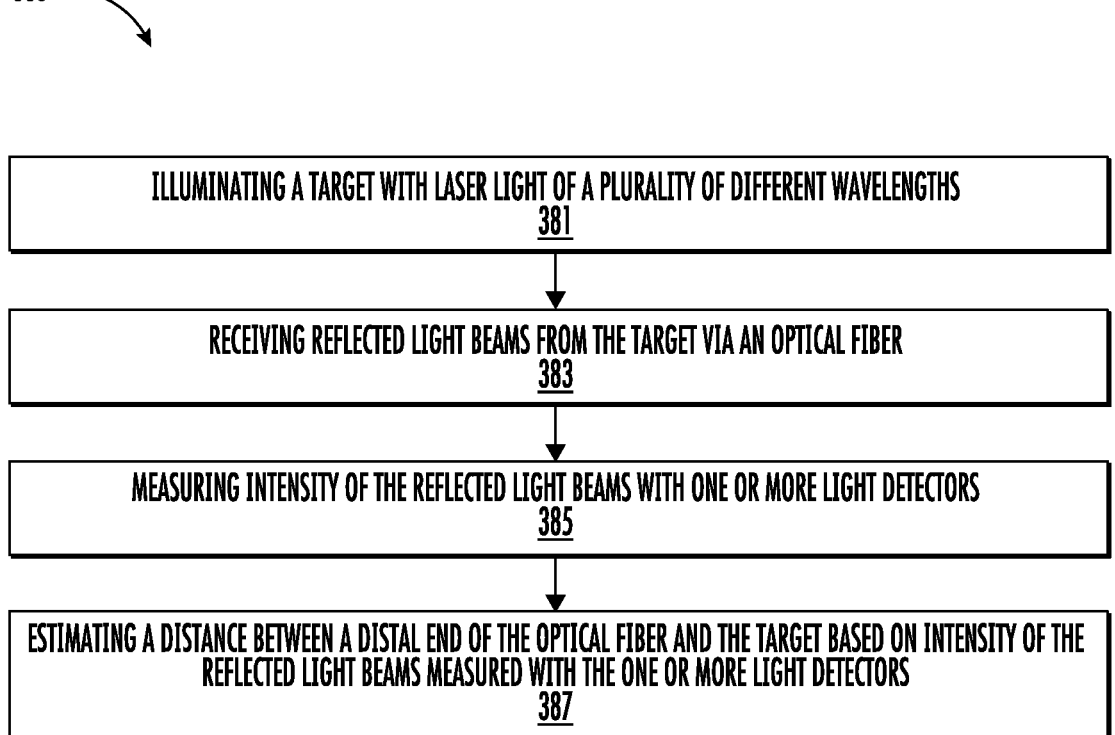

ILLUMINATING A TARGET WITH LASER LIGHT OF A PLURALITY OF DIFFERENT WAVELENGTHS
381

RECEIVING REFLECTED LIGHT BEAMS FROM THE TARGET VIA AN OPTICAL FIBER
383

MEASURING INTENSITY OF THE REFLECTED LIGHT BEAMS WITH ONE OR MORE LIGHT DETECTORS
385

ESTIMATING A DISTANCE BETWEEN A DISTAL END OF THE OPTICAL FIBER AND THE TARGET BASED ON INTENSITY OF THE REFLECTED LIGHT BEAMS MEASURED WITH THE ONE OR MORE LIGHT DETECTORS
387

FIG. 3C

METHOD AND SYSTEM FOR ESTIMATING DISTANCE BETWEEN A FIBER END AND A TARGET

This application claims the benefit of priority under 35 U.S.C. § 119 to U.S. Provisional Application No. 63/118, 857, titled "Method and System for Estimating Distance Between a Fiber End and a Target", filed on Nov. 27, 2020, the entirety of which is incorporated herein by reference.

This application claims the benefit of priority under 35 U.S.C. § 119 to U.S. Provisional Patent Application No. 63/118,117, titled "Apparatus and Method for Enhancing Laser Beam Efficacy in a Liquid Medium", filed on Nov. 25, 2020, the entirety of which is incorporated herein by reference.

This application claims the benefit of priority under 35 U.S.C. § 119 to U.S. Provisional Patent Application No. 63/252,830, titled "Method and System for Estimating Distance Between a Fiber End and a Target", filed on Oct. 6, 2021, the entirety of which is incorporated herein by reference.

TECHNICAL FIELD

The present disclosure generally relates to the field of optical fibers used in medical or therapeutic laser deliver. Particularly, but not exclusively, the present disclosure relates to a method and system for estimating distance between a fiber end and a target.

BACKGROUND

Introduction of lasers into the medical field and the development of fiber optic technologies that use lasers has opened numerous applications in treatments, diagnostics, therapies, and the like. Such applications range from invasive and non-invasive treatments to endoscopic surgeries and image diagnostics. For instance, in urinary stone treatment, the stones are required to be fragmented into smaller pieces. A technology known as laser lithotripsy may be used for such fragmenting processes, wherein for small to medium sized urinary stones, a rigid or flexible ureteroscope is placed through the urinary tract for illumination and imaging. Simultaneously, an optical fiber is inserted through a working channel of the ureteroscope, to a target location (e.g., to the location where the stone is present in the bladder, ureter, or kidney). The laser is then activated to fragment the stone into smaller pieces or to dust it. In another instance, a laser and optic fiber technology is used in coagulation or ablation treatments. During an ablation treatment, laser light is delivered to the tissue to vaporize the tissue. During a coagulation treatment, laser light is used to induce thermal damage within the tissue. Such ablation treatments may be used for treating various clinical conditions, such as Benign Prostate Hyperplasia (BPH), cancers such as prostate cancer, liver cancer, lung cancer and the like, and for treating cardiac conditions by ablating and/or coagulating a part of the tissue in the heart.

These treatments which use laser and optic fiber technology require high amounts of accuracy to ensure that the laser is aimed at the right target (stone, tissue, tumor etc.), to achieve the clinical objective of tissue ablation, coagulation, stone fragmentation, dusting and the like. Accordingly, it is important to know the distance between the target and end of the optical fiber (distal end) where the laser light is emitted, since the laser treatment parameters, such as energy, pulse width, laser power modulation, and/or repetition rate, are often determined based on the distance between the tip of the optical fiber to the target.

One of the existing techniques to estimate the distance between the distal end of an optical fiber and a target provides for measuring and comparing intensity values of reflections of the light beams, where the light beams are transmitted through the optical fiber by modulating the numerical apertures of the light beams. However, it is not always convenient to shift the numerical apertures of the light beams. Moreover, separation of the reflection of light beams of different numerical apertures, required for these techniques is difficult.

BRIEF SUMMARY

This Summary is provided to introduce a selection of concepts in a simplified form that are further described below in the Detailed Description. This Summary is not intended to necessarily identify key features or essential features of the claimed subject matter, nor is it intended as an aid in determining the scope of the claimed subject matter.

In one aspect, the present disclosure relates to a system comprising first and second laser sources, an optical fiber, a light detector, and a processor and memory. The first laser source may generate laser light of a first wavelength and the second laser source may generate laser light of a second wavelength. The optical fiber may have a distal end and be configured to pass laser light from the first and second laser sources out of the distal end and to receive reflected laser light into the distal end. The light detector may measure intensity of the reflected light. The processor and memory may include instructions that when executed by the processor cause the processor to estimate a distance between the distal end of the optical fiber and a target based on the intensity of the reflected light measured by the light detector.

In some embodiments, the first wavelength has a first water absorption coefficient higher than a second water absorption coefficient of the second wavelength. In some such embodiments, the ratio of the first water absorption coefficient to the second water absorption coefficient is at least 2 to 1. In further such embodiments, the first wavelength is approximately 1330 nm to approximately 1380 nm and the second wavelength is approximately 1260 nm to approximately 1320 nm. Still further embodiments include a third laser source to generate laser light of a third wavelength utilized to characterize a condition of the optical fiber, wherein the third wavelength has a third water absorption coefficient higher than the first and the second water absorption coefficients. In a further embodiment, the third wavelength comprises approximately 1435 nm, approximately 2100 nm, or a wavelength between approximately 1870 nm and approximately 2050 nm.

In some embodiments, the light detector measures a first intensity value of the reflected light corresponding to the laser light of the first wavelength and a second intensity value of the reflected light corresponding to the laser light of the second wavelength. In some such embodiments, the instructions, when executed by the processor, further cause the processor to compute a ratio of the first intensity value and the second intensity value; and estimate the distance between the distal end of the optical fiber and the target based on the ratio of the first intensity value and the second intensity value.

In various embodiments, one or more of the first and second laser sources comprise a polarization maintaining pigtailed fiber laser, a single mode pigtailed fiber laser, or a free space laser.

Several embodiments include a wave division multiplexer (WDM) coupled to a proximal end of the optical fiber, the WDM to arrange the laser light of the first wavelength and the laser light of the second wavelength to enter a proximal end of the optical fiber at one or more of a same point and a same angle.

In another aspect, the present disclosure relates to at least one non-transitory computer-readable medium comprising a set of instructions that, in response to being executed by a processor circuit, cause the processor circuit to perform one or more of: determine a first intensity value based on first reflected laser light corresponding to laser light of a first wavelength, wherein the laser light of the first wavelength exits a distal end of an optical fiber and the first reflected laser light is reflected by a target and enters the distal end of the optical fiber; determine a second intensity value based on second reflected laser light corresponding to laser light of a second wavelength, wherein the laser light of the second wavelength exits the distal end of the optical fiber and the second reflected laser light is reflected by the target and enters the distal end of the optical fiber; compute a ratio of the first intensity value and the second intensity value; and estimate a distance between the distal end of the optical fiber and the target based on the ratio of the first intensity value and the second intensity value.

In some embodiments, the set of instructions, in response to execution by the processor circuit, further cause the processor circuit to subtract a first internal reflection value from a first measured intensity value to determine the first intensity value and subtract a second internal reflection value from a second measured intensity value to determine the second intensity value.

In various embodiments, the set of instructions, in response to execution by the processor circuit, further cause the processor circuit to determine an internal reflection value based on third reflected laser light corresponding to laser light of a third wavelength, wherein the laser light of the third wavelength exits a laser source and the at least a portion of the third reflected laser light is reflected by a distal end of the optical fiber. In various such embodiments, the set of instructions, in response to execution by the processor circuit, further cause the processor circuit to compare the internal reflection value to a baseline internal reflection value; and adjust an operating parameter of a treatment beam based on comparison of the internal reflection value to the baseline internal reflection value. In further such embodiments, the set of instructions, in response to execution by the processor circuit, further cause the processor circuit to compare the internal reflection value to a baseline internal reflection value; characterize a condition of the optical fiber based on comparison of the internal reflection value to the baseline internal reflection value; and communicate an indication of the condition of the optical fiber via a user interface.

In some embodiments, the set of instructions, in response to execution by the processor circuit, further cause the processor circuit to communicate an indication of the distance estimated between the distal end of the optical fiber and the target via a user interface.

In yet another aspect, the present disclosure may include a method, comprising one or more of: illuminating a target with laser light of a plurality of different wavelengths; receiving reflected light beams from the target via an optical fiber; measuring intensity of the reflected light beams with one or more light detectors; and estimating a distance between a distal end of the optical fiber and the target based on intensity of the reflected light beams measured with the one or more light detectors.

In some embodiments, the method includes emitting the laser light of the plurality of different wavelengths via the optical fiber to illuminate the target.

In various embodiments, the method includes measuring a first intensity value of the reflected light beams corresponding to laser light of a first wavelength and a second intensity value of the reflected light beams corresponding to laser light of a second wavelength. In various such embodiments, the method includes computing a ratio of the first intensity value and the second intensity value; and estimating the distance between the distal end of the optical fiber and the target based on the ratio of the first intensity value and the second intensity value.

BRIEF DESCRIPTION OF THE DRAWINGS

Non-limiting embodiments of the present disclosure are described by way of example with reference to the accompanying figures, which are schematic and not intended to be drawn to scale. In the figures, each identical or nearly identical component illustrated is typically represented by a single numeral. In will be appreciated that various figures included in this disclosure may omit some components, illustrate portions of some components, and/or present some components as transparent to facilitate illustration and description of components that may otherwise appear hidden. For purposes of clarity, not every component is labelled in every figure, nor is every component of each embodiment shown where illustration is not necessary to allow those of ordinary skill in the art to understand the disclosure. In the figures:

FIGS. 3A-3C illustrate flowcharts showing methods of estimating distance between a fiber end and a target in accordance with some embodiments of the present disclosure.

DESCRIPTION OF THE DISCLOSURE

Figure 1A:
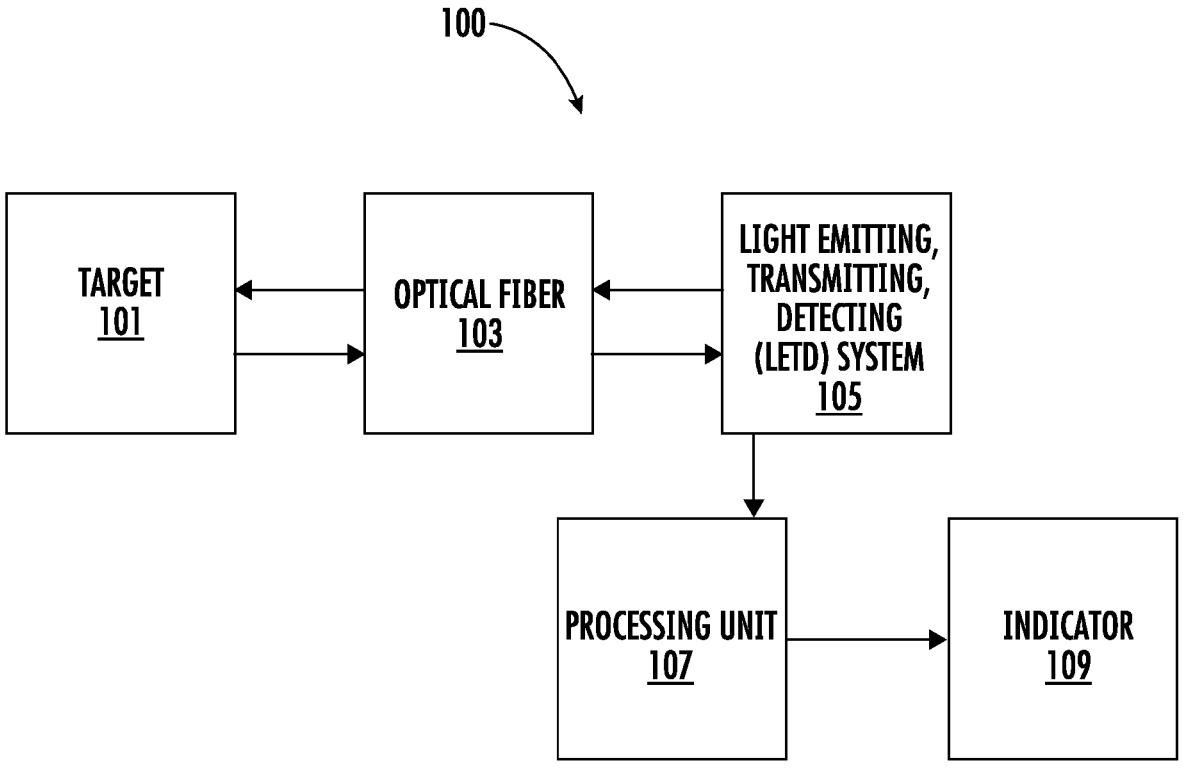
FIG. 1A illustrates an exemplary architecture for estimating distance between a fiber end and a target in accordance with some embodiments of the present disclosure.

The present disclosure provides a method and system for estimating the distance between an optical fiber end and a target. It is to be appreciated that the efficiency of treatments using lasers often depend upon the relative position and orientation of the optical fiber tip with respect to the target. However, due to various factors such as movement of the optical fiber with respect to position and orientation within the body of a subject (for instance, a patient), tissue environment, movement of the tissue, surface of the target, color of the target, pigment of the target, optical fiber tip degradation during a treatment, water irrigation, and turbid environment (e.g., due to dusting), and the like, it is extremely difficult to determine or estimate the distance between the optical fiber tip and the target. Determining the distance between the optical fiber tip and the target is further complicated by the fact that the optical fiber tip is typically inserted into the body of the subject.

Incorrect estimation of the distance between the fiber end and the target and incorrect estimation of the orientation of the fiber end can lead to aiming the laser at a region which is not the region of interest of the target. This may lead to unnecessary complications, and in some cases it can also lead to permanent damage to certain parts of the tissues, organs, etcetera of the subject, which could make portions of the body the subject dysfunctional. In some other scenarios, incorrect distance measurement and orientation may lead to an increase in the duration of the treatment, or may lead to low quality ablation/fragmentation results. In some cases, such as BPH or cancer, if the tumor is not ablated properly, it may lead to regrowth of the tumor (or other undesired tissue) leading to further complications. Therefore, it is important to determine an accurate (or maintain a desired) distance between the optical fiber tip and the target while performing certain treatments using laser and optical fiber technology as discussed above.

The method includes illuminating, by a light emitting, transmitting, and detecting (LETD) system, a target with laser light of different wavelengths having low and high water absorption coefficients, using different laser light sources. The wavelengths may be selected in such a way that, they are close to each other and belong to the same "nm scale." Further, the LETD system receives returned signals corresponding to the incident laser light of different wavelengths. The returned signals comprise light beams reflected from the target post illumination. The one or more light detectors configured in the LETD system may detect the returned signals to measure intensity values of the returned signals of a specific wavelength. Using the measured intensity values, a processing unit may then estimate the distance between the fiber end and the target.

The present disclosure uses the described LETD system in different configurations comprising different arrangements of various optical components, such as beam combiners, beam splitters, polarizers, collimators, wave division multiplexers (WDM), light detectors and the like. The present disclosure enables accurate estimation of the distance between a fiber end and a target. Additionally, the present disclosure provides a robust distance estimation technique that is compatible with different types of targets. Further, the present disclosure may be used for the purpose of controlling and/or adjusting one or more operational parameters. For instance, during a treatment, the target may move around, back, and forth or otherwise, or may change one or more of its shape, size, composition, pigment, and color. Therefore, parameters for the laser sources that are pre-set before initiating lasing on the target, may become less effective. Conventionally, such pre-set parameters are manually changed, which may be error prone and time consuming, or in some cases the pre-set parameters may be left unchanged which may lead to scenarios where the optical fiber may be too close or too far from the target. Therefore, the present disclosure allows automatic and real-time monitoring of the distance between the optical fiber end and the target, and further enables automatically changing of the pre-set lasing parameters to adjust the lasing in accordance with the target shape, position etc. and to provide a higher likelihood of achieving the desired result or outcome from the treatment.

The foregoing has broadly outlined the features and technical advantages of the present disclosure such that the following detailed description of the disclosure may be better understood. It is to be appreciated by those skilled in the art that the embodiments disclosed may be readily utilized as a basis for modifying or designing other structures for carrying out the same purposes of the present disclosure. The novel features of the disclosure, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present disclosure.

Figure 1B:
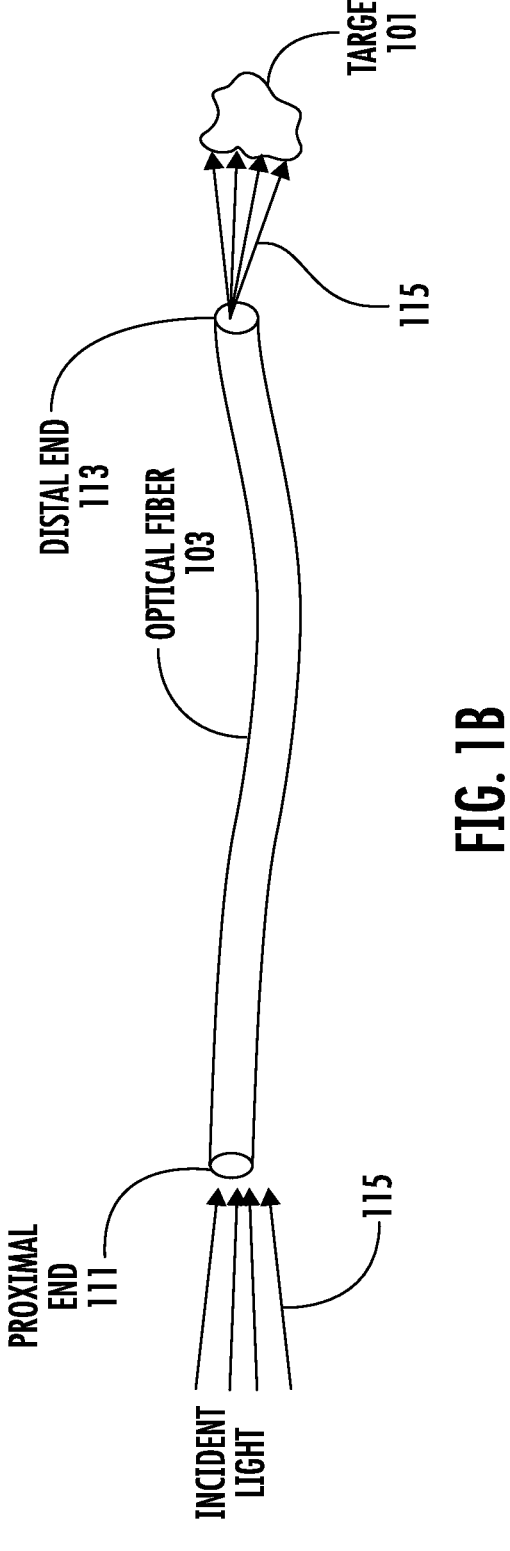
FIG. 1B illustrates an exemplary optical fiber in accordance with some embodiments of the present disclosure.

FIG. 1A shows an exemplary architecture 100 for estimating a distance between a fiber end and a target in accordance with some embodiments of the present disclosure. In some embodiments, the exemplary architecture 100 comprises a target 101, an optical fiber 103, a light emitting, transmitting, and detecting (LETD) system 105, a processing unit 107 and an indicator 109. In some embodiments, the target 101 may be a tissue, a stone, a tumor, a cyst, and the like, within a subject, which is to be treated, ablated, or destroyed. In some embodiments, the subject may be a human being or an animal. Further, the optical fiber 103 comprises a proximal end and a distal end. The proximal end is the end of the optical fiber 103 through which light beams enter the optical fiber 103 and the distal end is the end of the optical fiber 103 through which the light beams are emitted and can be directed onto the target 101. Therefore, the light beams 115 enter at the proximal end 111 of the optical fiber 103, propagate through length of the optical fiber 103, exit from the distal end 113, and are directed onto (or towards) the target 101 from the distal end 113 of the optical fiber 103, as shown in the FIG. 1B.

In some embodiments, the light beams may be beams directed from a light source. For example, the light source can be a laser light source. As an example, the laser light sources may include, but is not limited to, solid-state lasers, gas lasers, diode lasers, and fiber lasers. The light beams may include one or more of an aiming beam, a treatment beam, and any other beam transmitted through the optical fiber 103. In various embodiments, an aiming beam may include a light beam of low intensity that is transmitted through the optical fiber 103 to estimate the distance between the optical fiber end (e.g., the distal end 113) and the target 101. In several embodiments, a treatment beam may include a light beam of high intensity that is transmitted through the optical fiber 103 to treat the target 101. In some embodiments, the different light beams may be produced by one or more laser light sources. As a specific example, the aiming beam may be generated by one laser source and the treatment beam may be generated by another laser source. In another example, both the aiming beam and the treatment beam may be generated by a single laser source. With yet another example, different laser light sources may be used to generate light beams of different wavelengths, characteristics, and the like.

Further, the optical fiber 103 may be associated with the LETD system 105 as shown in the FIG. 1A, to receive the light beams, to be aimed at the target 101, and to deliver the reflected light beams that reflect from the surface of and region around the target 101. In some embodiments, the optical fiber 103 may be optically, mechanically, and/or electrically coupled with the LETD system 105 via a port (not shown in the FIG. 1A).

In some embodiments, the LETD system 105 comprises optical components which may include, but are not limited to, one or more of laser light sources, polarizers, beam splitters, beam combiners, light detector, wavelength division multiplexers, collimators, circulators, that are configured in various combinations, as explained in detail in further parts of the present disclosure.

In many embodiments, laser light sources are configured to generate laser light beams, such as a low intensity aiming beam for the purpose of aiming the light beams 115 at the target 101 and a high intensity treatment beam for treating the target 101, and/or light beams with varying characteristics (e.g., intensities, wavelengths, etcetera) based on the application. Each laser light source may be configured to generate laser light having different wavelengths, where each of the different wavelengths can have different water absorption coefficients. Further, each laser light source may have the same aperture or different apertures. In some embodiments, each laser light source may be designated with a different purpose, for instance, one laser light source may be configured to generate aiming beams of a particular intensity and one laser light source may be configured to generate a treatment beam of a particular intensity, and one or more laser light sources may be configured to generate light beams of a specific wavelength having specific water absorption coefficient. Additionally, each laser light source may be configured to generate polarized laser light or unpolarized/depolarized light.

Polarizers may include the optical components that act as an optical filter. For example, polarizers may be configured to allow light beams of a specific polarization to pass through, and to block the light beams of different polarizations. Therefore, when undefined light (or light beams of mixed polarity) are provided as input to a polarizer, the polarizer provides a well-defined single polarized light beam as an output.

Beam splitters may include the optical components used to split incident light at a designated ratio into two separate beams. Further, beam splitters may be arranged to manipulate light to be incident at a desired angle of incidence (AOI). Therefore, in many embodiments, a beam splitter can be primarily configured with two parameters, a ratio of separation and an AOI. The ratio of separation comprises the ratio of reflection to transmission (reflection/transmission (R/T) ratio) of the beam splitter. Accordingly, as used herein, if the ratio of separation for a beam splitter is indicated as 50:50, it means that the beam splitter splits the incident light beams in a R/T ratio of 50:50. In other words, the beam splitter splits the incident light beams by changing the incident light by reflecting 50 percent and transmitting the other 50 percent. Further, as an example, if the AOI for the beam splitter is indicated as 45 degrees, it means that the beam splitter ensures that the light beams would be incident at an angle of 45 degrees. Beam splitters may include, but are not limited to, polarizing beam splitters and non-polarizing beam splitters. Polarizing beam splitters may split incident light based on the S-polarization component and P-polarization component, such as, for example by reflecting the S-polarized component of light and transmitting the P-polarized component of light (or vice-versa). In some embodiments, non-polarizing beam splitters may split incident light beams based on a specific R/T ratio while maintaining the original polarization state of the incident light beams.

Beam combiners may include partial reflectors that combine two or more wavelengths of light, such as by using the principle of transmission and reflection as explained above. In many embodiments, a beam combiner may be a combination of beam splitters and mirrors, which perform the functionality of combining light of two or more wavelengths.

Light detectors may include devices that detect and/or measure characteristics of light beams and encode the detected and/or measured characteristics in electrical signals. For example, light detectors may detect the specific type of light beams (as preconfigured), and convert the light energy associated with the detected light beams into electrical signals. In some embodiments, wavelength division multiplexing may include a technology that combines a number of optical carrier signals onto a single optical fiber while using laser lights of different wavelengths.

A collimator may include a device that narrows down light beams. To narrow down the light beam, a collimator may be configured to cause the directions of motion to become more aligned in a specific direction (for example, parallel rays), or to cause the spatial cross section of the beam to become smaller. In many embodiments, a collimator may be used to change diverging light from a point source into a parallel beam.

A circulator may include a multi-port optical device configured to receive and emit light via a predetermined sequence of the multiple ports. For example, a circulator may include a three (or four, or five, etc.) port optical device designed such that, light entering any one port exits from the next port. In one such example, light entering a first port may exit a second port, light entering the second port may exit a third port, and light entering the third port may exit the first port. Oftentimes circulators may be utilized to allow light beams to travel in only one direction.

It is noted that where optical component described herein list specific parameters, such as, a beam splitter having an R/T ratio of 50:50 and an AOI of 45 degrees, these parameters are provided for general understanding of the concepts disclosed and not to be limiting. As a specific example, a beam splitter could be provided in various embodiments described herein having a different R/T ratio and/or AOI than specified here without departing from the scope of the disclosure and claims. In one such example, an AOI of 40 degrees may be utilized. In another such example an R/T ratio of 47:53 may be utilized.

The LETD system 105 is further associated with a processing unit 107 via a communication network. In some embodiments, the communication network may be a wired communication network or a wireless communication network. The processing unit 107 may be configured to receive measured values from the LETD system 105 and estimate the distance between the distal end of the optical fiber 103 and the target 101. In some embodiments, the processing unit 107 may be a standalone device with the processing capability required for distance estimation. For example, processing device 107 can include circuitry arranged to determine a distance based on electrical signals received from the LETD system 105. As another example, processing device 107 can include circuitry and memory comprising instructions, which when executed by the circuitry cause the circuitry to determine a distance based on electrical signals received from the LETD system 105. Still, in some other embodiments, the processing unit 107 may be a computing device such as a laptop, a desktop, a mobile phone, a tablet phone, and the like, configured to perform the distance estimation using their processing capability.

The processing unit 107 may be associated with the indicator 109 to indicate the estimated distance between the distal end of the optical fiber 103 and the target 101. The indicator 109 may include, but not limited to, a visual indicator which displays the estimated distance, an audio indicator which announces the estimated distance, or a haptic indicator which indicates the estimated distance via vibration patterns. In various embodiments, the indicator may be presented via a graphical user interface and/or overlaid on a graphical representation, such as a video feed. In some embodiments, the computing device configured as the processing unit 107 may be configured to perform the functionalities of the indicator 109. In some other embodiments, the indicator 109 may be a standalone device which is configured to indicate the estimated distance between the distal end of the optical fiber 103 and the target 101.

Various exemplary configurations for estimating distance between the fiber end and the target are explained in detail below. However, values and parameters associated with different optical components used in each of the below explained configurations, should be considered purely exemplary, and not be construed as a limitation of the present disclosure.

FIG. 2A through FIG. 2G illustrate example configuration of portions of architecture 100 including numerous configurations for the LETD system 105. It is noted that often the description of a prior figure (e.g., FIG. 2A) is relied on to fully describe another figure (e.g., FIG. 2E, for example). However, examples are not limited in this respect.

Figure 2A:
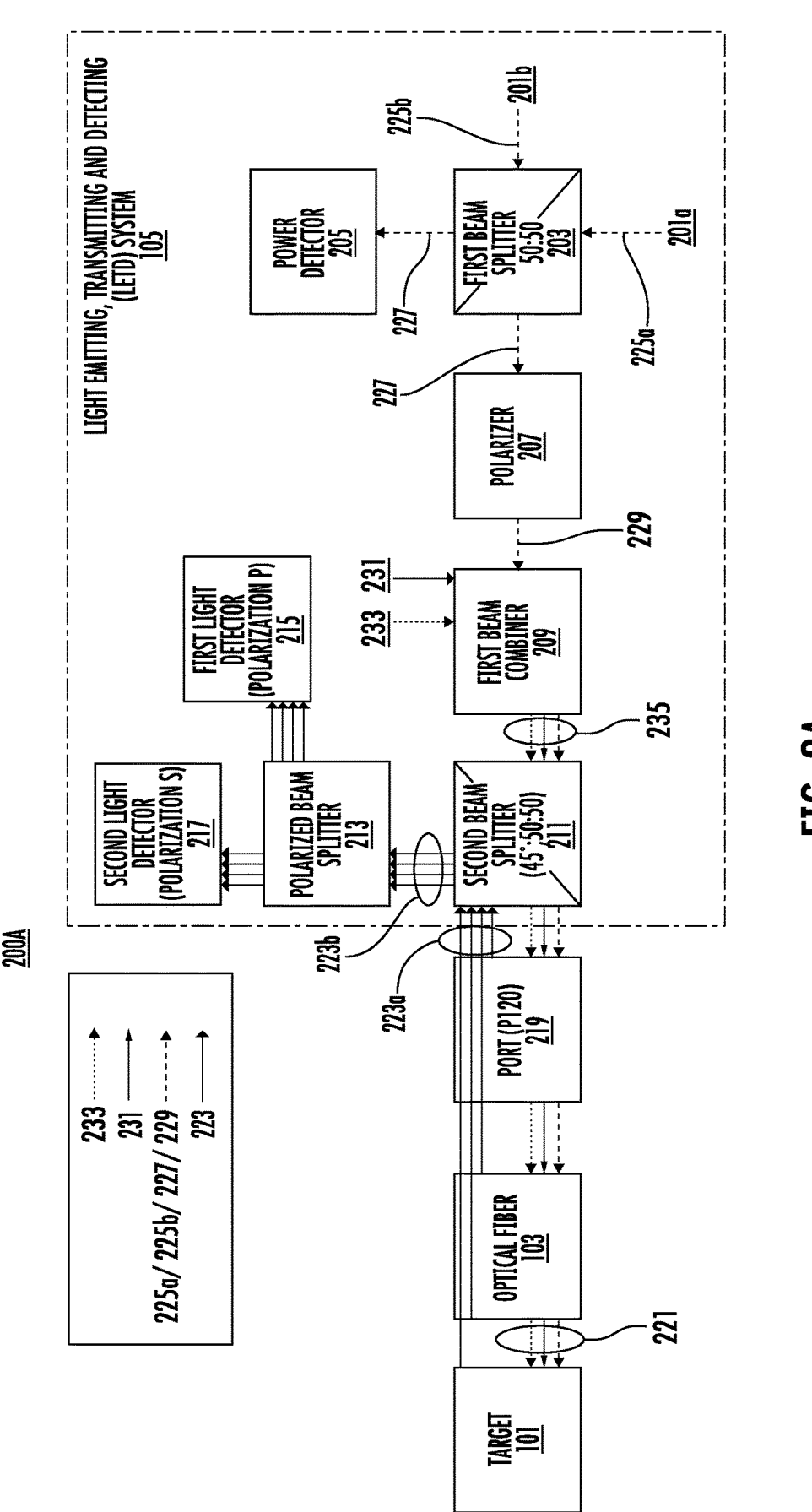
FIGS. 2A-2G illustrate exemplary configurations for estimating distance between a fiber end and a target in accordance with some embodiments of the present disclosure.

FIG. 2A illustrates an exemplary configuration 200A for estimating distance between a fiber end and a target in accordance with some embodiments of the present disclosure. In configuration 200A, the LETD system 105 may include one or more polarized (or non-polarized) lasers, one or more beam splitters, a polarizer, a beam combiner, and one or more light detectors. The one or more beam splitters may be polarized beam splitters, non-polarized beam splitters or a combination of both polarized and non-polarized beam splitters. As shown in the FIG. 2A, the LETD system 105 includes a first polarized laser source 201a, a second polarized laser source 201b, a first beam splitter 203, a power detector 205, a polarizer 207, a first beam combiner 209, a second beam splitter 211, a polarized beam splitter 213, a first light detector 215, and a second light detector 217.

In configuration 200A, the first polarized laser source 201a is arranged to generate laser light 225a (or light beam 225a) with a wavelength having a high water absorption coefficient relative to the wavelength of laser light 225b generated by the second polarized laser source 201b. As used herein, the laser light 225a generated by the first polarized laser source 201a can be referred to as high water absorption coefficient light (HI) while the laser light 225b generated by the second polarized laser source 201b can be referred to as low water absorption coefficient light (LO). It is to be appreciated that even though the terms "high" and "low" are used they are intended to be interpreted relative to each other, or in the alternative relative to a threshold characteristic describing the water absorption of a particular wavelength. For example, a high water absorption characteristic can be greater than or equal to 50% while a low water absorption characteristic can be less than or equal to 50%.

In various embodiments, the ratio of the high water absorption coefficient to the low absorption coefficient may be approximately 1:2. For example, laser light 225a may utilize a wavelength of approximately 1310 nm and have a water absorption coefficient of approximately 0.1651 while laser light 225b may utilize a wavelength of approximately 1340 nm and have a water absorption coefficient of approximately 0.333. The higher the ratio between the high and low absorption coefficients may result in less sensitivity to system noise (e.g., electrical, or opto-mechanical noise), but the resulting system may not be effective at distances over 3 mm. The lower the ratio between the high and low absorption coefficients may result in higher sensitivity to system noise, but the resulting system may remain effective up to distances of 5 or 6 mm. In some examples, the first and second polarized laser sources 201a and 201b may be polarization maintaining (PM) pigtailed fiber lasers.

The laser sources 201a and 201b are associated with and in optical communication with the first beam splitter 203. Said differently, the laser beams 225a and 225b generated by laser sources 201a and 201b, respectively, are provided as input to the first beam splitter 203, which is configured to split the incident light beams 225a and 225b at a ratio of approximately 50:50 (e.g., 47:53 or 49:51), such that the incident light beams 225a and 225b align along a single optical path as light beam 227. However, it will be appreciated that any ratios between 99:1 and 1:99 may be utilized without departing from the scope of this disclosure. Similarly, although AOIs of 45 degrees may be described in embodiments, it will be appreciated that any AOIs between 1 and 89, such as 43-47 degrees, 40 degrees, or 20 degrees, may be utilized without departing from the scope of this disclosure.

The power detector 205 is associated with and in optical communication with the first beam splitter 203. The power detector 205 is arranged to measure the optical power in the optical signal (e.g., the portion of the light beams 225a and 225b routed to the power detector 205) corresponding to each wavelength of light in the light beam 227. In some embodiments, the term "optical power" may refer to energy transported by a certain laser beam, per unit time.

The first beam splitter 203 is further associated with an in optical communication with the polarizer 207. The first beam splitter is further arranged to provide a portion of the light beams 225a and 225b, denoted as light beam 227, which is aligned along a single optical path, as an input to the polarizer 207. In some embodiments, the polarity of the polarizer 207 may be pre-configured. The polarizer 207 is associated with and in optical communication with the first beam combiner 209. As such a manner, the polarized light 229 obtained as an output from the polarizer 207 is provided as input to the first beam combiner 209.

The first beam combiner 209 may combine the polarized light beams 229 with an aiming beam 231 and a treatment beam 233 into a combined light beam 235, as shown in the FIG. 2A. In some other embodiments, the aiming beam 231 and the treatment beam 233 may be generated by one or more laser sources (not shown) other than the laser sources 201a and 201b. As an example, the treatment beam 233 may be generated by a solid-state laser or a fiber laser, such as a holmium (HO) laser. However, this should not be considered as a limitation of the present disclosure, since the treatment beam may be generated by lasers other than a HO laser, such as Neodymium, Erbium, Thulium, and the like. In some other embodiments, the aiming beam 231 and the treatment beam 233 may be generated by the laser sources 201a and 201b. The combined light beam 235, comprising the aiming beam 231, treatment beam 233, and the polarized light beams 229 from laser sources 201a and 201b, may be subjected to the second beam splitter 211 having a configuration of a 50:50 R/T ratio and a 45-degree AOI. That is, first beam combiner 209 can be associated with an in optical communication with the second beam splitter 211 such that the combine light beam 235 is provided as input to the second beam splitter 211.

The second beam splitter 211 may split the combined light beam 235 in the ratio of 50:50, such that, the aiming beam 231, the treatment beam 233, and the polarized light beams 229 from laser sources 201a and 201b are aligned along a single optical path. The second beam splitter 211 is optically coupled to the optical fiber 103 (e.g., via the port 219, or the like) such that a portion of the light beam 235, which is the output of the second beam splitter 211 is transmitted through the optical fiber 103 (e.g., via the port 219) as shown in the FIG. 2A and denoted as light beams 221. The light beams 221 are transmitted to the proximal end 111 of the optical fiber 103, which then propagate through the length of the optical fiber 103 to be delivered to the target 101 from the distal end 113 of the optical fiber 103. As an example, the target 101 may be a tissue, a stone, a tumor, a cyst, and the like, within a subject, which is to be treated, ablated, destroyed, or the like.

When the light beams 221 are delivered to the target 101 via the optical fiber 103, the target 101 may reflect some portion of the incident light beams 221 away from the optical fiber 103 and some portion of the light towards the optical fiber 103, wherein the portion of light reflected towards the optical fiber 103 may re-enter the optical fiber 103, at the distal end of the optical fiber 103. The portion of the reflected light re-entering at the distal end may be referred as reflected light 223a. The reflected light 223a may be transmitted "backward" in the optical fiber 103 from the distal end to the proximal end of the optical fiber 103. When the reflected light 223a reaches the proximal end of the optical fiber 103, the reflected light 223a may be subjected to the second beam splitter 211. The reflected light 223a may include numerous reflections, such as from the proximal end of the optical fiber 103, from the distal end of the optical fiber 103, from the port 219, and the like, due to which the reflected light 223a is no longer polarized.

To polarize the reflected light 223a, the reflected light may be first subjected to the second beam splitter 211 to align the optical path of the reflected light 223a and then subjected to the polarized beam splitter 213. The reflected light 223a would be incident at an angle of 45 degrees to the second beam splitter 211 and split in the ratio of 50:50 (or another ratio as outlined hereby). The reflected light 223b which emerges out of the second beam splitter 211 is thereafter subjected to the polarized beam splitter 213 as shown in the FIG. 2A. The polarized beam splitter 213 may split the reflected light 223b into reflected P-Polarized and transmitted S-polarized beams. In some embodiments, the first light detector 215 may be configured to detect the P-polarized beams of the light 223b reflected by the polarized beam splitter 213 while the second light detector 217 may be configured to detect the S-polarized beams of the light 223b transmitted by the polarized beam splitter 213. The first light detector 215 and the second light detector 217 may measure intensities of the detected light beams of the light 223b, respectively, and transmit the intensities to the processing unit 107. In some embodiments, the processing unit 107 may estimate distance between the distal end of the optical fiber 103 and the target 101 based on the measured intensities. The method of estimating the distance between the distal end of the optical fiber 103 and the target 101 based on the measured intensities is explained in greater detail below with respect to FIGS. 3A-3C.

Figure 2B:
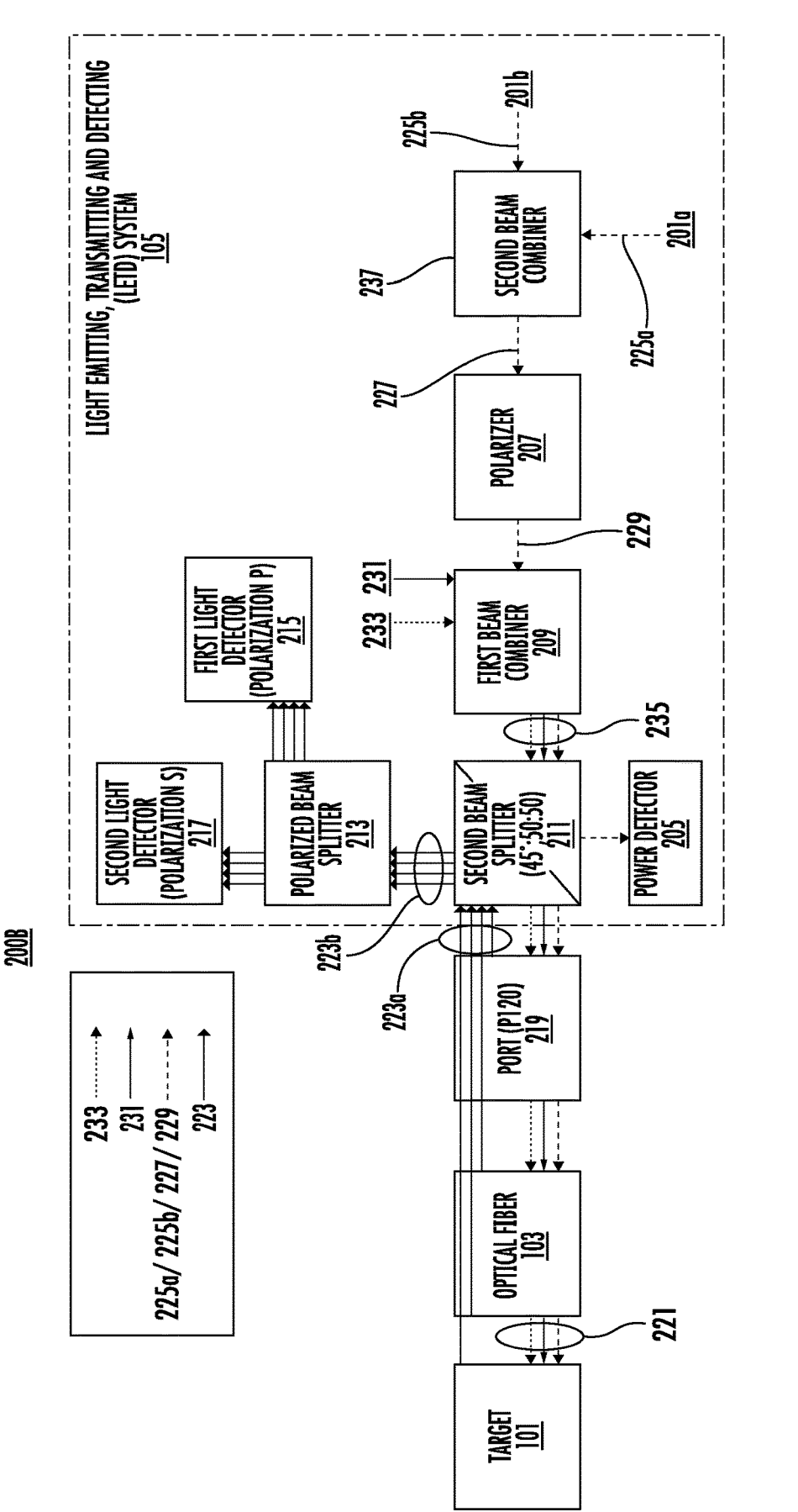

FIG. 2B shows an exemplary configuration 200B for estimating distance between a fiber end and a target in accordance with some embodiments of the present disclosure. Configuration 200B, is different from configuration 200A in two constructional aspects. One of the constructional aspects which is different in configuration 200B when compared to configuration 200A is the arrangement of the first beam splitter 203. In configuration 200B, the first beam splitter 203 is replaced with a second beam combiner 237. Since the first beam splitter 203 is replaced with a second beam combiner 237, the power detector 205, which was associated with the first beam splitter 203 in configuration 200A, is arranged to be associated with the second beam splitter 211 in configuration 200B. Embodiments are not limited in this context.

In configuration 200B, the LETD system 105 may include one or more polarized lasers, one or more beam splitters, a polarizer, one or more beam combiners, and one or more light detectors. The one or more beam splitters may be polarized beam splitters, non-polarized beam splitters, or a combination of both polarized and non-polarized beam splitters. As shown in FIG. 2B, the LETD system 105 the polarized laser source 201a, the polarized laser source 201b, the power detector 205, the polarizer 207, the first beam combiner 209, the second beam combiner 237, the second beam splitter 211, the polarized beam splitter 213, the first light detector 215, and the second light detector 217. In this configuration, as shown in the FIG. 2B, the polarized laser source 201a has a wavelength with high water absorption coefficient (HI) and the polarized laser source 201b has a wavelength with low water absorption coefficient (LO).

The incident light beams from laser sources 201a and 201b are provided as input to the second beam combiner 237, which is configured to combine the incident light beams 225a and 225b that are generated by the laser sources 201a and 201b into light beam 227. Further, the output of the second beam combiner 237 (e.g., light beam 227) can be provided as an input to the polarizer 207 for providing the polarized light beam 229 as an output. In some embodiments, the polarization of the polarizer 207 may be pre-configured. Thereafter, the polarized light 229 obtained as an output from the polarizer 207 may be provided as input to the first beam combiner 209. The first beam combiner 209 may combine the polarized light beams 229 with the aiming beam 231 and the treatment beam 233 into combined light beam 235, as shown in the FIG. 2B.

The combined light beam 235 comprising the aiming beam 231, the treatment beam 233, and the polarized light beams 229 from laser sources 201a and 201b, may be subjected to the second beam splitter 211 having a configuration of an R/T ratio of 50:50 and an AOI of 45-degree (or any other R/T ratio and AOI as outlined hereby). The second beam splitter 211 may split the combined light beam 235 in the ratio of 50:50, such that, the aiming beam 231, the treatment beam 233, and the polarized light beams 229 from laser sources 201a and 201b, may be aligned along a single optical path.

The power detector 205 associated with the second beam splitter 211 may measure the power in the optical signal (the light beam 235, the light beam 229, or the like) corresponding to each wavelength. In various embodiments, the power detector 205 may detect cumulative energy of the optical signal received at the second beam splitter 211. In some embodiments, the term "optical power" may refer to energy transported by a certain laser beam, per unit time. The light beams 221, which are the output of the second beam splitter 211, are then transmitted to the optical fiber 103 (e.g., via a port 219) as outlined above with respect to FIG. 2A.

Additionally, reflected light 223a and received and processed as outlined above with respect to FIG. 2A.

Figure 2C:
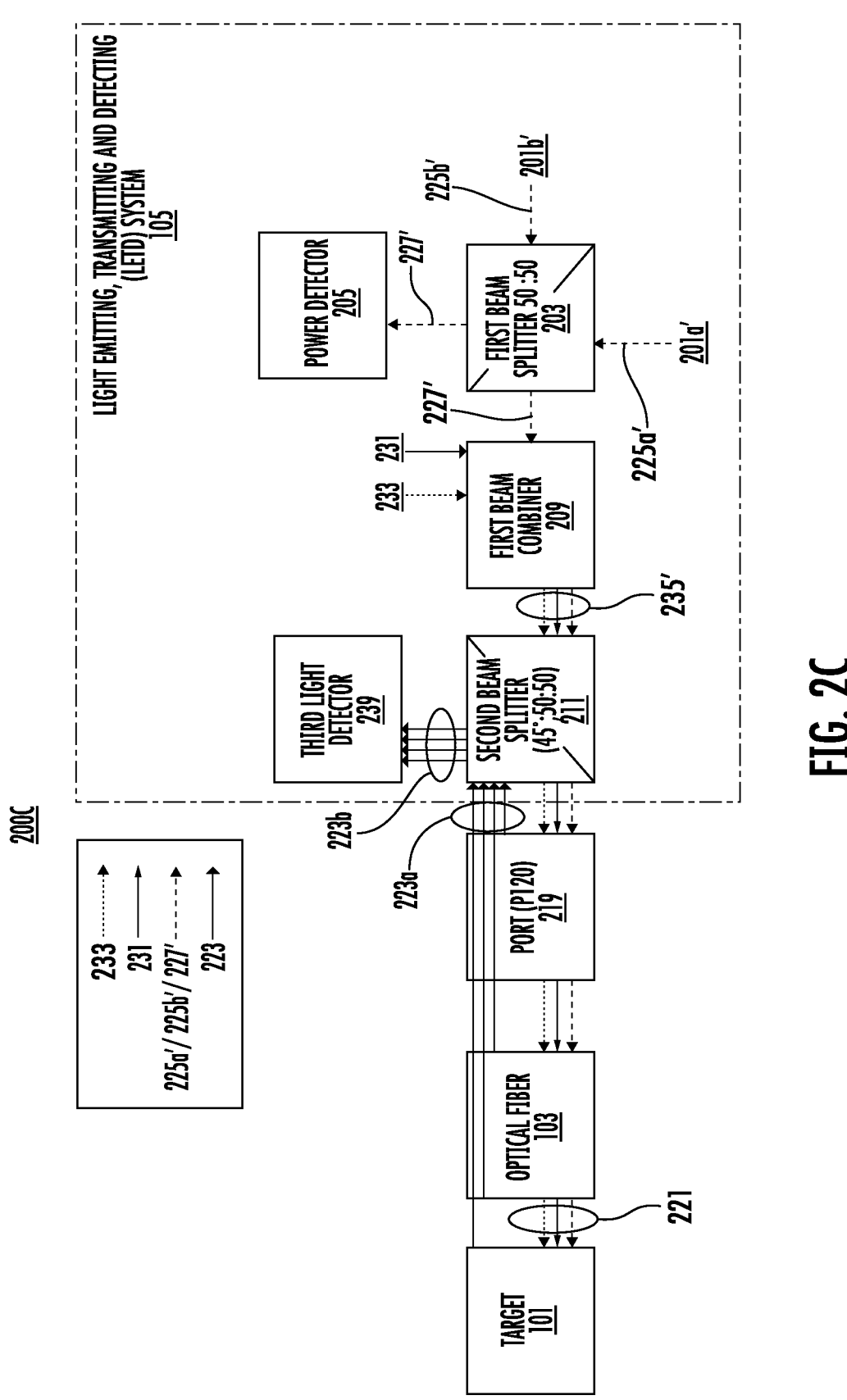

FIG. 2C shows an exemplary configuration 200C for estimating distance between a fiber end and a target in accordance with some embodiments of the present disclosure. The present disclosure can work with polarized and non-polarized laser sources. Accordingly, in configuration 200C, the laser sources 201a' and 201b' used for providing incident light beams (source light) are non-polarized laser sources. As an example, the laser sources 201a' and 201b' may be Single Mode (SM) fiber pigtailed lasers. When the laser sources 201a' and 201b' are non-polarized laser sources, there is no requirement of the polarizer 207, the polarized beam splitter 213, the first light detector 215 for detecting P-polarized light beams and the second light detector 217 for detecting S-polarized light beams, as depicted in configurations 200A and 200B described above.

In configuration 200C, the LETD system 105 may include one or more non-polarized lasers, one or more beam splitters, a beam combiner, and a light detector. The one or more beam splitters may be non-polarized beam splitters. As shown in the FIG. 2C, the LETD system 105 includes a first non-polarized laser source 201a', a second non-polarized laser source 201b', the first beam splitter 203, the power detector 205, the first beam combiner 209, the second beam splitter 211, and a third light detector 239.

Like the prior configurations, in the configuration 200C, the non-polarized laser source 201a' can have a wavelength with high water absorption coefficient (HI) while the non-polarized laser source 201b' can have a wavelength with low water absorption coefficient (LO). The incident light beams 225a' and 225b' from laser sources 201a' and 201b' are provided as input to the first beam splitter 203 which is configured to split the incident light beams at a ratio of 50:50, in a way that, the incident light beams 225a' and 225b' align along a single optical path as light beams 227'.

The power detector 205 associated with the first beam splitter 203 may measure the power in the optical signal (light beam 227') corresponding to each wavelength. Since, configuration 200C is implemented in a non-polarized environment, polarization based optical components, such as, a polarizer and a polarized beam splitter are not needed in this configuration. Therefore, the output of the first beam splitter 203, which is the incident light 225a' and 225b' aligned along a single optical path as light 227', may be provided as an input to the first beam combiner 209. The first beam combiner 209 may combine the light beams 227' coming from the first beam splitter 203 with the aiming beam 231 and the treatment beam 233, as shown in the FIG. 2C.

In some embodiments, the aiming beam 231 and the treatment beam 233 may be generated by one or more laser sources other than the laser sources 201a' and 201b'. In some other embodiments, the aiming beam 231 and the treatment beam 233 may be generated by the laser sources 201a' and 201b'. The combined light beam 235' comprising the aiming beam 231, the treatment beam 233 and the non-polarized light beams 201a' and 201b' from laser sources 201a' and 201b', may be subjected to a second beam splitter 211 having a configuration of ratio 50:50 and AOI of 45 degree (or any other R/T ratio and AOI as outlined hereby). The second beam splitter 211 may split the combined light beam 235' in the ratio of 50:50, such that, the aiming beam 231, the treatment beam 233 and the non-polarized light beams 225a' and 225b' are aligned along a single optical path. The light beams 221 which are the output of the second beam splitter 211, are then transmitted to an optical fiber 103 (e.g., via a port 219) while reflected light 223a is transmitted backwards, as shown in the FIG. 2C and described above.

Since, configuration 200C is implemented in a non-polarized environment, the reflected light 223a is only subjected to the second beam splitter 211 to align the optical path of the reflected light 223a while a polarized beam splitter, as depicted in configurations 200A and 200B is not needed. The reflected light 223a would be incident at an angle of 45 degrees to the second beam splitter 211 and split in the ratio of 50:50. The reflected light 223b which emerges out of the second beam splitter 211 may be directly detected by a single detector. As such, the configuration 200C provides the third light detector 239.

The third light detector 239 may measure intensity of the detected light beams of the reflected light 223b, respectively, and transmit the intensity to the processing unit 107. In some embodiments, the processing unit 107 may estimate the distance between the distal end of the optical fiber 103 and the target 101 based on the measured intensities. The method of estimating the distance between the distal end of the optical fiber 103 and the target 101 based on the measured intensities is explained in greater detail below with respect to FIGS. 3A-3C.

Figure 2D:
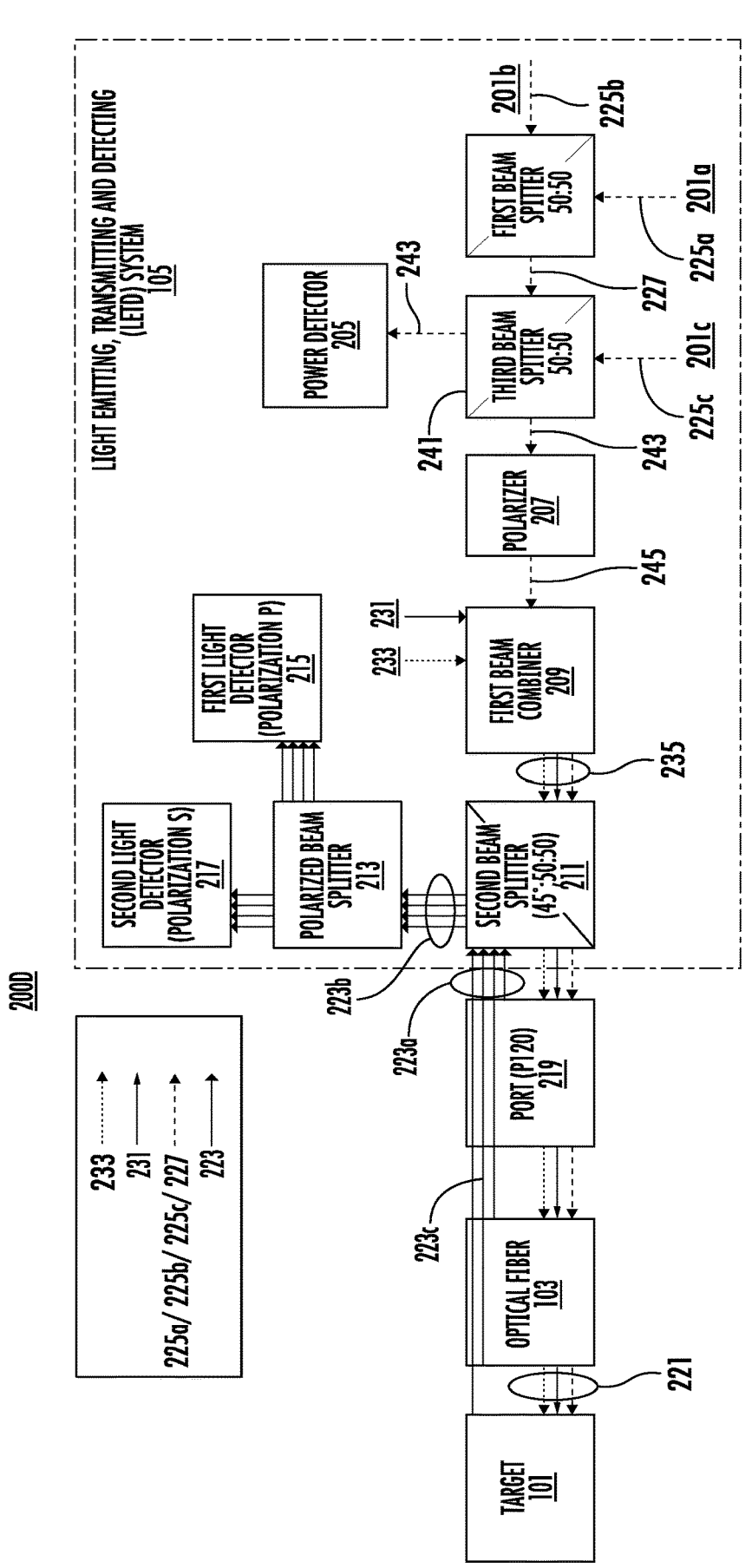

FIG. 2D shows an exemplary configuration 200D for estimating distance between a fiber end and a target in accordance with some embodiments of the present disclosure. The configuration 200D comprises a third polarized laser source 201c, which is introduced for the purpose of calibration of the optical fiber condition in real-time. As an example, the condition of the optical fiber 103 may include, but is not limited to, any changes or degradation of the distal or proximal ends of the optical fiber 103, fiber bending effects on polarization scrambling, or any other degradations and changes occurring in the optical fiber 103. Changes in condition of the optical fiber 103, specifically the tips/ends (e.g., the input and output facets) of the optical fiber 103 may adversely affect the transmitted and reflected light beams, causing large number of reflections, loss of energy and inaccurate measurements. This can affect the accuracy of the distance estimation, thereby leading to incorrect positioning of the optical fiber 103 during a treatment.

In configuration 200D, the LETD system 105 may include one or more polarized lasers, one or more beam splitters, a polarizer, a beam combiner, and one or more light detectors. The one or more beam splitters may be polarized beam splitters, non-polarized beam splitters, or a combination of both polarized and non-polarized beam splitters. As shown in the FIG. 2D, the LETD system 105 includes the polarized laser source 201a, the polarized laser source 201b, and the polarized laser source 201c, the first beam splitter 203, the power detector 205, the polarizer 207, the first beam combiner 209, the second beam splitter 211, the polarized beam splitter 213, the first light detector 215, the second light detector 217, and a third beam splitter 241. In configuration 200D, as shown in the FIG. 2D, the incident light beams 225a and 225b from laser sources 201a and 201b are provided as input to the first beam splitter 203, which is configured to split the incident light beams 225a and 225b at a ratio of 50:50, such that the incident light beams 225a and 225b align along a single optical path forming light beams 227. Further, the output of the first beam splitter 203, which is the incident light beams 225a and 225b aligned along a single optical path (e.g., light beams 227) can be provided as an input to the third beam splitter 241, which is also configured to split the incident light beams in the ratio of 50:50 forming light beams 243 that comprise light 225a, 225b, and 225c.

At the third beam splitter 241, incident light beams 225c from the polarized laser source 201c (e.g., light meant for calibration) are provided as input along with the output of the first beam splitter 203 (e.g., light beams 227). The power detector 205 associated with the third beam splitter 241 may measure the power in the optical signal (e.g., light beam 243) corresponding to each wavelength arriving at the third beam splitter 241. Along with the output of the first beam splitter 203, the third beam splitter 241 receives incident light beams from the polarized laser source 201c.

In some embodiments, the polarized laser source 201c has a wavelength with a very high water absorption co-efficient (e.g., substantially, completely, or almost completely, absorbed by water) relative to the wavelength of light emitted by the laser source 201a and 201b. As an example, the wavelength of the polarized laser source 201c may be approximately 1435 nm and have a water absorption coefficient of approximately 31.55 (or approximately 100 times the "high" water absorption source). At a distance of 0.5 mm with a wavelength of 1435 nm about 98-99% of the light is absorbed. In some embodiments, the calibration light source may have a wavelength of approximately 1420 to approximately 1440 (resulting in a water absorption coefficient of approximately 30. Alternative, or additional, wavelengths with a very high water absorption coefficient may be utilized (e.g., 1870-2070 nm). However, the further the wavelength is from the HI and LO wavelengths (e.g., 1310 nm and 1340 nm, respectively) may lead to a more complicated optical design. For example, a detector may cover range of approximately 1100-1600 nm, and if the very high water absorption coefficient laser has a wavelength of 2000 nm, a unique, or additional, detector would be required. In some embodiments, the calibration laser may have a wavelength of approximately 1435 nm, approximately 2100 nm, or a wavelength between approximately 1870 nm and approximately 2050 nm.

Based on the readings of the polarized laser source 201c (e.g., as measured by the power detector 205) the processing unit 107 may define an optical baseline characteristic of the "quality" of fiber tip at the distal end 113 of the optical fiber 103. More specifically, as the laser source 201c is highly absorbed in water, light from the laser source 201c will not likely reach the target tissue, and as a result hardly any light from the laser source 201c will be reflected back into the optical fiber 103 as part of the reflected light 223a. Therefore, the component of light reflections 223c with the wavelength of light associated with the laser source 201c are mainly attributable to the optical characteristics of distal end 113 of the optical fiber 103. It is to be appreciated that the distal end 113 of the optical fiber 103 goes through degradation during a laser treatment due to, for example, heat and cavitation. In many embodiments, increased intensity readings of back reflected light 223c may indicate optical fiber tip degradation. In several embodiments, at a certain threshold of intensity changes from the baseline reading for a specific fiber (e.g., 10% to 50%, greater than or equal to 25%, 50%, 75%, 90%, between 10% and 100%, or the like) the processing unit 107 may indicate that the optical fiber 103 should be checked or replaced, such as through a user interface and/or audible alarm. In addition, optical fiber tip degradation may cause higher internal reflections from the distal end of the fiber, of light from polarized laser sources 201a and 201b. Whether or not the laser sources are polarized may have minimal effect on internal reflections because the light is randomly depolarized in the fiber. However, monitoring the reflections from the fiber distal end by the very high absorption coefficient laser (e.g., 1435 nm laser)

can be utilized to determine changes in distal end reflections (in percentage of initial reflections of 1435 versus real-time reflections). Further, the changes in distal end reflections may applied on the initial reflections from the distal end for the LO laser (e.g., 1310 nm laser) and HI laser (e.g., 1340 nm laser) to update the initial reflections.

Moreover, fiber tip degradation may change the ratios between polarities P and S in back reflected light 223a or 223c. Therefore, creating baseline readings, for a specific optical fiber 103 currently in use, and monitoring these baselines on the fly, may allow more accurate distance estimations even when and during the tip of the fiber degrades and until degradation reaches a threshold level that indicates that the optical fiber 103 should be replaced. Further, output of the third beam splitter 241, or light beams 243, which includes the incident light beams 225a, 225b and 225c that are aligned along a single optical path, may be provided as an input to the polarizer 207 to obtain a single polarized light beam 245 as an output. In some embodiments, the polarization of the polarizer 207 may be pre-configured.

The polarized light 245 obtained as an output from the polarizer 207 can be provided as input to the first beam combiner 209. The first beam combiner 209 may combine the polarized light beams 245 with the aiming beam 231 and the treatment beam 233 to form combined light beam 235 as shown in FIG. 2D. As detailed above, the aiming beam 231 and/or the treatment beam 233 may be generated by one or more laser sources other than the laser sources 201a, 201b, or 201c or the aiming beam 231 and/or the treatment beam 233 may be generated by the laser sources L1 and L2.

The combined light beam 235 comprising the aiming beam 231, the treatment beam 233 and the polarized light beams 245 may be subjected to the second beam splitter 211 having a configuration of ratio 50:50 and a 45-degree AOI. The second beam splitter 211 may split the combined light beam 235 in the ratio of 50:50, such that, the aiming beam 231, the treatment beam 233, and the polarized light beams 245 are aligned along a single optical path. The light beams 221, which are the output of the second beam splitter 211, are then transmitted to optical fiber 103 (e.g., via port 219).

Figure 2E:
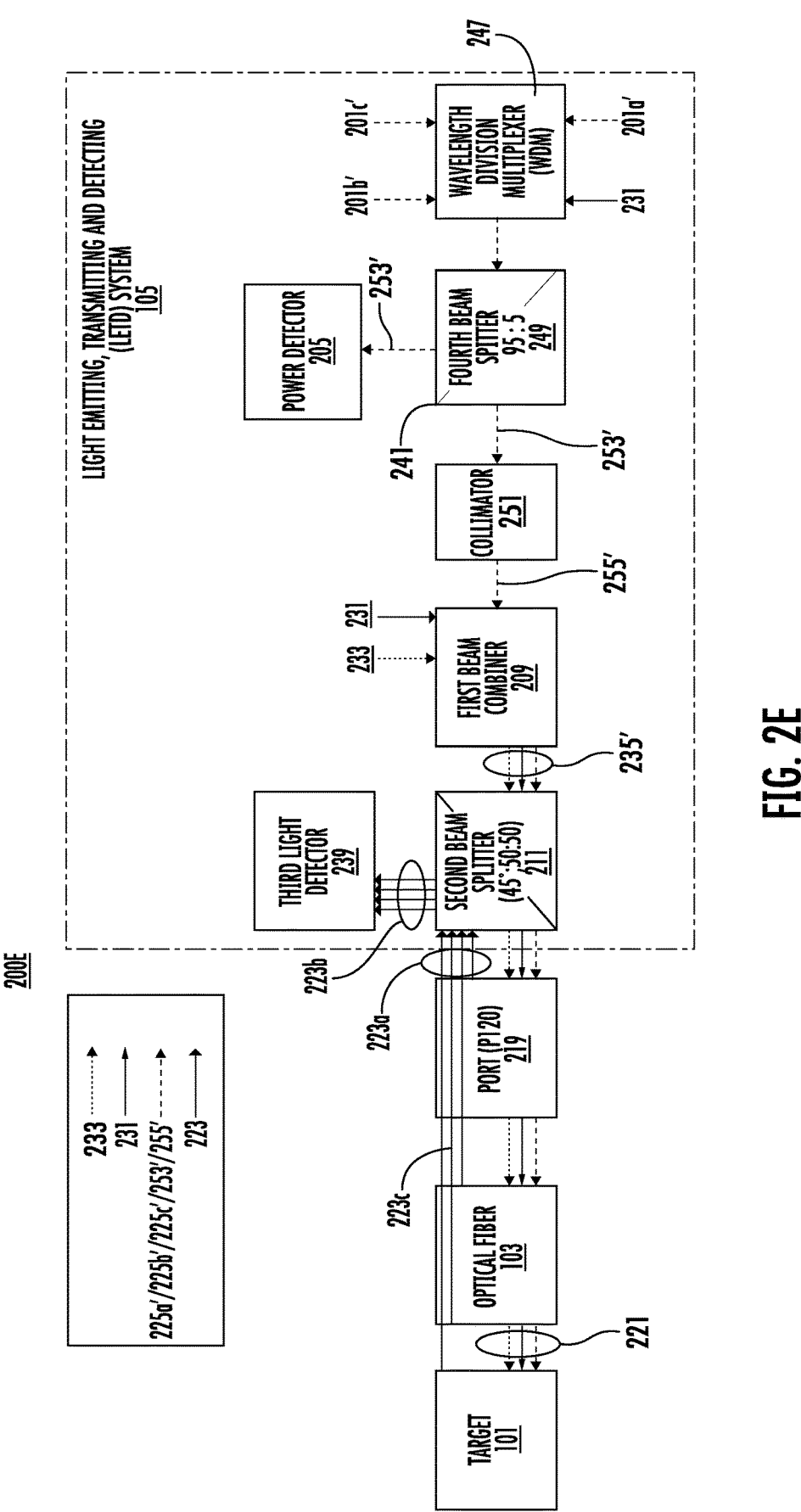

FIG. 2E shows an exemplary configuration 200E for estimating distance between a fiber end and a target in accordance with some embodiments of the present disclosure. Configuration 200E, like configuration 200C, is implemented in a non-polarized environment. Further, configuration 200E is a "semi-fiber based design" in which the two input beam splitters seen in the previous configurations (e.g., the configuration 200D) are replaced with a wavelength division multiplexer (WDM). The WDM power loss may be approximately 20% while the beam splitter power loss may be approximately 50%, improving efficiency of the LETD system 105 with use of the WDM. Additionally, the WDM may perfectly, or almost perfectly, align each of the three laser sources into an optical path. However, beam splitters and beam combiners are considerably less accurate at aligning each of the three laser sources into a single beam.

Configuration 200E utilizes a third non-polarized laser 201c' along with the first non-polarized laser 201a' and the second non-polarized laser 201b'. The third non-polarized laser 201c' is introduced for the purpose of calibration of the optical fiber condition in real-time as described above. In will be appreciated that the calibration laser may be polarized, or non-polarized, without departing from the scope of this disclosure. In configuration 200E, the LETD system 105 may include one or more non-polarized lasers, one or more beam splitters, a beam combiner, one or more light detectors, a WDM, and a collimator. As shown in the FIG. 2E, the LETD system 105 includes the non-polarized laser source 201*a'*, the non-polarized laser source 201*b'*, the non-polarized laser source 201*c'*, the power detector 205, the first beam combiner 209, the second beam splitter 211, the third light detector 239, a WDM 247, a fourth beam splitter 249 and a collimator 251. In configuration 200E, the non-polarized laser source 201*a'* can emit light with a wavelength having a high water absorption coefficient (HI) while the non-polarized laser source 201*b'* can emit light with a wavelength having a low water absorption coefficient (LO). Further, the non-polarized laser source 201*c'* can emit light having a wavelength with a very high water absorption co-efficient (e.g., completely, or almost completely, absorbed by water) relative to the wavelength of light emitted by the laser sources 201*a'* and 201*b'*. As an example, the wavelength of the non-polarized laser source (L3') may be 1435 nm.

As mentioned above, in configuration 200E, the first beam splitter 203 and the third beam splitter 241 shown in FIG. 2D are replaced with the WDM 247. In some embodiments, to ensure correct usage of the non-polarized laser source 201*c'* as a real-time calibrator, the incident light beams coming from each of the non-polarized lasers 201*a'*, 201*b'* and 201*c'* can be arranged to enter at the proximal end of the optical fiber 103 at the same point and at the same angle. In many embodiments, it may be difficult or impossible to align incident light beams from each of the non-polarized lasers 201*a'*, 201*b'* and 201*c'* to enter at the same point and at the same angle with combiners/splitters. To ensure adherence with this condition of same point and same angle, configuration 200E utilizes WDM 247. The WDM 247 can be configured to ensures that all the incident light beams coming from each of the non-polarized lasers 201*a'*, 201*b'* and 201*c'* enter at the proximal end of the optical fiber 103 at the same point and at the same angle. Moreover, in various embodiments, usage of WDM 247 may lower power loss, such as when compared to some beam splitters which cause 50%-75% power loss.

The incident light beams from 201*a'*, 201*b'*, 201*c'* and an aiming beam 231 are provided as inputs to the WDM 247, which is configured to combine the incident light beams in a way that the light beams move identically. Further, output of the WDM 247 may be provided as an input to a fiber-based beam splitter (e.g., the fourth beam splitter 249), which can be arranged to split the incident light beams at a high transmission to reflection ratio (e.g., 95:5 or 99:1), as shown in the FIG. 2E. In some embodiments, the fourth beam splitter 249 is a fiber-based beam splitter. The power detector 205 associated with the fourth beam splitter 249 may measure the power in the optical signal (e.g., light beam 253') corresponding to each wavelength. Further, the output of the fourth beam splitter 233 (e.g., light beam 253'), which is the incident light aligned along a single optical path, may be provided as an input to the collimator 251 to narrow down the light beams 253' into parallel beams.

Thereafter, output of the collimator 251 (e.g., light beams 255') can be provided to the first beam combiner 209, which combines the light beams 255' coming out of the collimator 251 with an aiming beam 231 and the treatment beam 233 as shown in FIG. 2E. In several embodiments, the aiming beam 231 may be introduced at the WDM 251. In many embodiments, the aiming beam 231 may be introduced at the first beam combiner 209. Still, in some embodiments, the aiming beam 231 can be introduced at both the WDM 251 and the first beam combiner 209. In some embodiments, the aiming beam 231 and/or the treatment beam 233 may be generated by one or more laser sources other than the laser sources 201*a'*, 201*b'* and 201*c'* or the aiming beam 231 and/or the treatment beam 233 may be generated by the laser sources 201*a'*, 201*b'* and 201*c'*.

The combined light beam 235' comprising the aiming beam 231, the treatment beam 233, and the light beams 255' (e.g., e.g., light from laser sources 201*a'*, 201*b'* and 201*c'* received from the first beam combiner 209) may be subjected to the second beam splitter 211 having a configuration of R/T ratio 50:50 and a 45-degree AOI. The second beam splitter 211 may split the combined light beam 235' in the ratio of 50:50, such that, the aiming beam 231, the treatment beam 233, and the non-polarized light beams 255' from laser sources 201*a'*, 201*b'* and 201*c'* may be aligned along a single optical path. The light beams 221, which are the output of the second beam splitter 211, are then transmitted to an optical fiber 103 (e.g., via port 219) as shown and more fully described above.

Figure 2F:
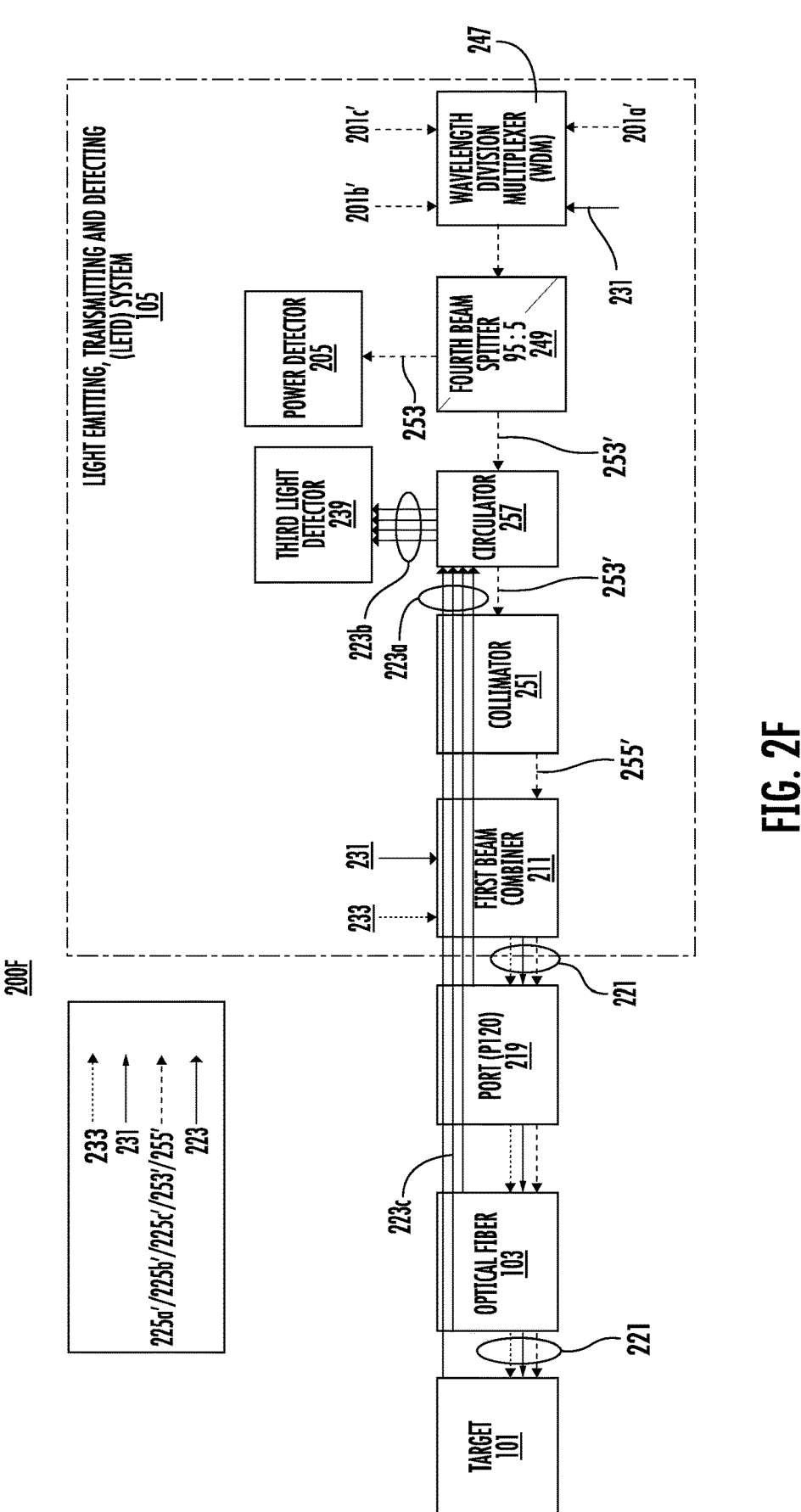

FIG. 2F shows an exemplary configuration 200F for estimating distance between a fiber end and a target in accordance with some embodiments of the present disclosure. Configuration 200F, like configuration 200C and 200E, is implemented with non-polarizing detectors. However, the sources can be non-polarized or polarized. In this exemplary configuration, the LETD system 105 may include one or more non-polarized lasers (or polarized lasers), one or more beam splitters, a beam combiner, one or more light detectors, a WDM, a circulator and a collimator. As shown in the FIG. 2F, the LETD system 105 includes the non-polarized laser source 201*a'*, the non-polarized laser source 201*b'*, the non-polarized laser source 201*c'*, the power detector 205, the first beam combiner 209, the third light detector 239, the WDM 247, the fourth beam splitter 249, the collimator 2251, and a circulator 257. In configuration 200F, the non-polarized laser source 201*a'* can emit light having a wavelength with a high water absorption coefficient (HI) while the polarized laser source 201*b'* can emit light having a wavelength with a low water absorption coefficient (LO). Further, the non-polarized laser source 201*c'* can have a wavelength with very high water absorption co-efficient, which is substantially absorbed in water.

As mentioned above, in configuration 200F, the first beam splitter 203 and the third beam splitter 241 as shown in FIG. 2D are replaced with the WDM 247 as shown in FIG. 2F. Further, in the exemplary configuration 200F, the second beam splitter 211 which was arranged to deliver the light beams to the port 219 in all the aforementioned exemplary configurations, is also eliminated. Beam splitters reduce output power by up to 50% (or more) and reduce an additional 50% (or more) of output power upon receiving return signals. Therefore, removal of the beam splitter in configuration 200F significantly increases the signal and the output power.

The incident light beams 225*a'*, 225*b'* and 225*c'* from laser sources 201*a'*, 201*b'* and 201*c'* as well as the aiming beam 231 are provided as inputs to the WDM 247, which is configured to combine the incident light beams in a way that the light beams move identically. Further, output of the WDM 231 may be provided as an input to the fourth beam splitter 249 that splits the incident light beams at a ratio of 95:5 as shown in the FIG. 2F. As previously mentioned, other ratios, such as 99:1, may be utilized without departing from the scope of this disclosure. In some embodiments, the fourth beam splitter 233 is a fiber-based beam splitter, thereby rendering configuration 200F an all fiber-based design. The power detector 205 associated with the fourth beam splitter 249 may measure the power in the optical signal (e.g., light beams 253') corresponding to each wavelength. Further, the output (e.g., the light beams 253') of the fourth beam splitter 249, which is the incident light aligned along a single optical path, may be provided as an input to the circulator 257. The circulator 257 is configured to ensures that all the light beams travel in one direction. Additionally, the circulator 257 provides the light beams 253' to the collimator 251, from a port other than the port into which the light beams 253' entered. The collimator 251 may narrow down the light beams into parallel beams 255'. The circulator 257 may, when compared to beam splitters, provide (1) lower power loses (beam splitter losses are ~50% in each direction) and (2) a more flexible optical design (free space optics require straight lines, while fiber based designs can be folded as desired).

Output (e.g., parallel light beams 255') of the collimator 251 may be provided to the first beam combiner 209, which combines the light beams 255' coming out of the collimator 251 with the aiming beam 231 and the treatment beam 233 into combined light beams 221, as shown in FIG. 2F. In some embodiments, the aiming beam 231 can either be introduced at the beginning (e.g., into the WDM 247), can be introduced at the first beam combiner 209, or can be introduced at both the WDM 247 and the first beam combiner 209. In some embodiments, the aiming beam 231 and/or the treatment beam 233 can be generated by one or more laser sources other than the laser sources 201a', 201b' and 201c' or the aiming beam 231 and/or the treatment beam 233 can be generated by the laser sources 201a', 201b', or 201c'. The combined light beam 221 comprising the aiming beam 231, the treatment beam 233, and the light beams 255' (e.g., light beams 225a', 225b' and 225c' from the laser sources 2901a', 201b' and 201c') received from the first beam combiner 209 may be transmitted to an optical fiber 103 (e.g., via a port 219), as shown in FIG. 2F. The combined light beams 221 are transmitted to the proximal end 111 of the optical fiber 103, which then propagate through the length of the optical fiber 103 and are delivered to the target 101 from distal end 113 of the optical fiber 103.

Figure 2G:
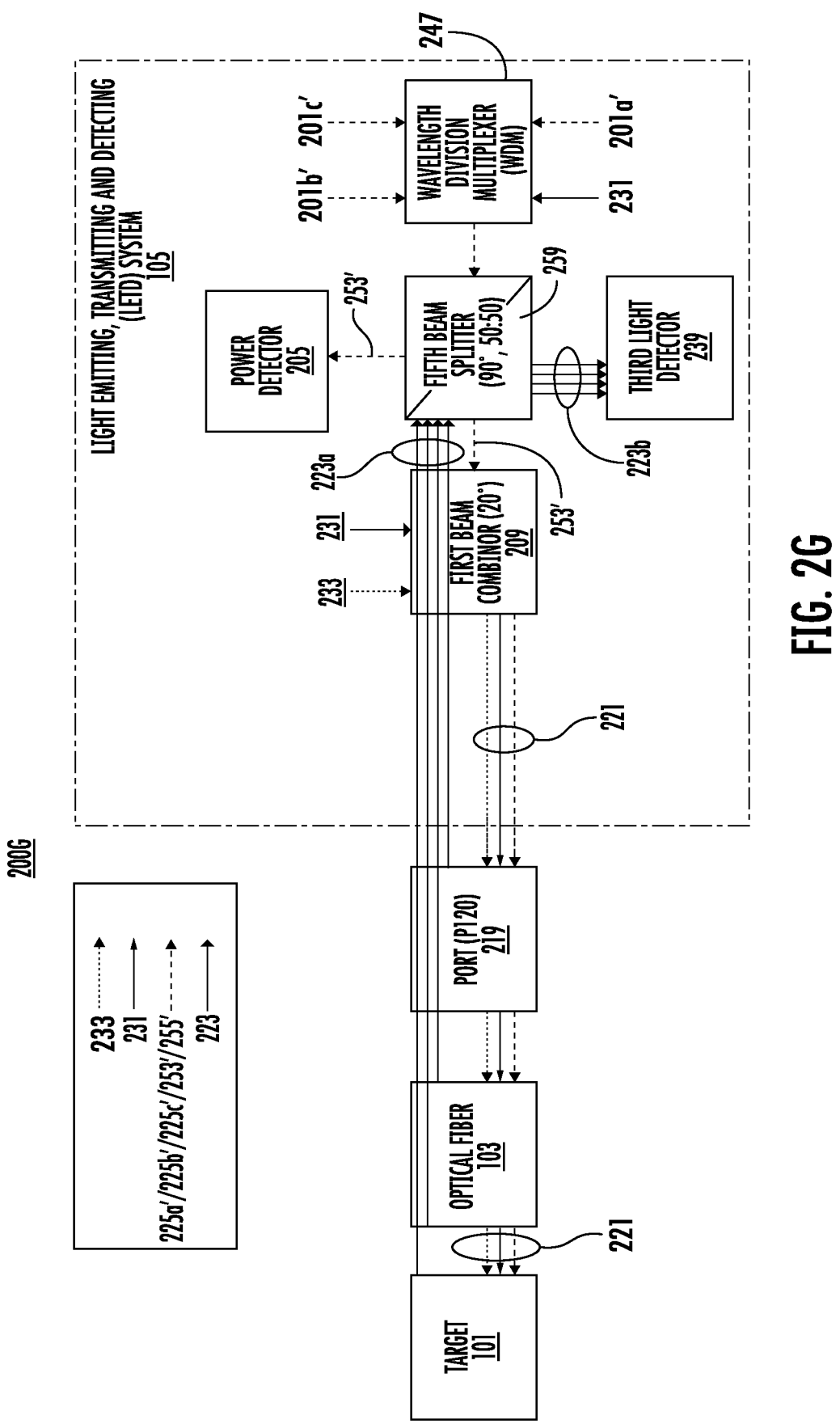

As outlined above, when the light beams 221 are delivered to the target 101 via the distal end 113 of the optical fiber 103, the target 101 may reflect some portion of light away from the optical fiber 103 and some portion of the light towards the optical fiber 103, wherein the portion of light reflected towards the optical fiber 103 may re-enter the optical fiber 103, at the distal end 113. The portion of the reflected light re-entering at the distal end 113, as outlined above, is referred to as reflected light 223a. The reflected light 223a may be transmitted "backward" through the optical fiber 103 from the distal end 113 to the proximal end 111. When the reflected light 223a reaches the proximal end 111 of the optical fiber 103, the reflected light 223a may pass through the first beam combiner 209 and the collimator 251 to be subjected to the circulator 251, where it is routed to the third light detector 239 and measured as described above. FIG. 2G shows exemplary configuration 200G for estimating distance between a fiber end and a target in accordance with some embodiments of the present disclosure. Configuration 200G, like some of the prior configurations, may be implemented in a non-polarized environment. In several embodiments, configuration 200G may include a single beam splitter based optical design. In configuration 200G, the WDM 247 can replace the function or operation of multiple beam splitters (e.g., ones utilized in configurations 200A-200D, or the like). The WDM 247 can receive input beams 225a', 225b' and 225c' from non-polarized laser sources 201a', 201b' and 201c'.

In configuration 200G, the LETD system 105 may include one or more non-polarized lasers (or polarized lasers), a beam splitter, a beam combiner, one or more light detectors, a WDM, and a collimator. As shown in FIG. 2G, the LETD system 105 includes the first non-polarized laser source 201a', the second non-polarized laser source 201b', the third non-polarized laser source 201c', the power detector 205, the first beam combiner 209, a fifth beam splitter 259, the third light detector 239, and the WDM 248. In configuration 200G, like in prior configurations, the non-polarized laser beam 225a' can have a wavelength with high water absorption coefficient (HI) relative to the non-polarized laser beam 225b', which itself can have a wavelength with a lower water absorption coefficient (LO). Further, the non-polarized laser beam 225c' can have a wavelength with a very high water absorption co-efficient as described in detail above.

As described above, processing unit 107 can, based on readings associated with reflections of light generated by the non-polarized laser source 201c', define an optical baseline characteristic of the quality of the distal end 113 of the optical fiber 103 (e.g., the output facet, or the like). More specifically, as light from laser source 201c' is highly absorbed in water, insignificant amounts of this light will be reflected back into the optical fiber 103 as part of the reflected light 223a. Therefore, readings associated with reflected light 223c are mainly attributable to the optical characteristics of the distal end 113 of the optical fiber 103, which as described goes through degradation during a laser treatment due to, for example, heat and cavitation. Accordingly, increased intensity readings of the back reflected light 223c may indicate optical fiber tip degradation.

In several embodiments, at a certain threshold of intensity changes from the baseline reading for a specific optical fiber 103 (e.g., 10% to 50%, greater than or equal to 25%, 50%, 75%, 90%, between 10% and 100%, or the like) the processing unit 107 may indicate that the optical fiber 103 should be checked or replaced, such as through a user interface and/or audible alarm. In addition, optical fiber tip degradation may cause higher internal reflections from the distal end 113 of the optical fiber 103, of light associated with non-polarized laser sources 201a' and 201b'. Moreover, fiber tip degradation may change the ratios between polarities P and S in back reflected light 223a or 223c. Therefore, creating baseline readings, for a specific optical fiber currently in use, and monitoring these baselines on the fly, may allow more accurate distance estimations even when and while the tip of the optical fiber degrades and until degradation reaches the point that an optical fiber should be replaced. Therefore greater dynamic control of parameters associated with a therapy or treatment can be provided.

Configuration 200G, like some prior configurations, utilizes WDM 247 to ensures that all the incident light beams coming from each of the non-polarized lasers 201a', 201b' and 201c' enter at the proximal end 111 of the optical fiber 103 at the same point and at the same angle. Moreover, in various embodiments, usage of WDM 247 may lower power loss, such as when compared to some configurations utilizing beam splitters.

The incident light beams 225a', 225b' and 225c' from laser sources 201a', 201b' and 201c' as well as the aiming beam 231 can be provided as inputs to the WDM 247, which can be configured to combine the incident light beams in a way that the light beams move identically. Further, output of the WDM 247 may be provided as an input to the fifth beam splitter 259, which can split the incident light beams at a ratio of 50:50 as shown in FIG. 2G. In some embodiments, the fifth beam splitter 259 may be a free space (e.g., glass)

based beam splitter. In some other embodiments, the fifth beam splitter 259 may be a fiber based beam splitter. In many embodiments, the power detector 205 associated with the fifth beam splitter 259 may measure the power in the optical signal (e.g., light beam 253') corresponding to each wavelength.

The output of the fifth beam splitter 259, which is the incident light aligned along a single optical path, may be provided as an input to the first beam combiner 209. The first beam combiner 209 may combine the light beams 253' coming out of the fifth beam splitter 259 with the aiming beam 231 and the treatment beam 233 as shown in FIG. 2G. In various embodiments, the aiming beam 231 may be introduced into the WDM 247, introduced at the first beam combiner 209, or introduced at both the WDM 247 and the first beam combiner 209. In several embodiments, the aiming beam 231 and/or the treatment beam 233 may be generated by one or more laser sources other than the laser sources 201a', 201b' and 201c' or the aiming beam 231 and/or the treatment beam 233 can be generated by the laser sources 201a', 201b' and 201c'. The combined light beam 221 comprising the aiming beam 231, the treatment beam 233, and the light beams 253' from laser sources 201a', 201b' and 201c' received from the first beam combiner 209 can be transmitted to the optical fiber 103 (e.g., via the port 219).

As can be seen from this figure, configuration 200G eliminates usage of a second beam splitter (e.g., the second beam splitter 211) and instead the fifth beam splitter 259, which was initially configured to split the incident light beams to align the incident light along a single optical path, is utilized to align the optical path of the reflected light 223a. Further, since configuration 200G utilizes a single beam splitter, it may be significantly less sensitive to treatment fiber movements and fiber bending radiuses, resulting in a more robust configuration. Moreover, since configuration 200G has fewer optical components, such as beam splitters, beam combiners, detectors, and the like, the configuration 200G may be more compact, simpler, and less expensive than other configurations.

In some embodiments, in each of the exemplary configurations described herein, the proximal end of optical fiber 103 may be coated with a special coating such as an anti-reflective (AR) coating. The AR coating can help in reducing noise created at the proximal end 111 of the optical fiber 103 and increase the dynamic range. In some embodiments, the light signal (e.g., reflected light beams 223) that enter the light detector may contain one or more of: (a) reflections from a port lens; (b) reflections from a blast shield; (c) reflections from the proximal end 111 of the optical fiber; and/or (d) reflections from the distal end 113 of the optical fiber.

In various embodiments, an AR coating for the blast shield may reduce reflections from the port lens to less than 1%, an AR coating for the port lens may reduce reflections from the blast shield to less than 1%, and an AR coating at the proximal end 111 of the optical fiber 103 may reduce reflections from the proximal end 111 of the optical fiber 103 from 3.5% down to approximately 0.5%. In some embodiments, the reflected signal from a target 101 such as stone, may be of very low energy, for instance nearly 1% of fiber output power where the distance from the optical fiber tip to the tissue is about 0 mm. By reducing the reflections from the proximal end 111 of the optical fiber 103 to nearly 0.5%, the present disclosure may help in improving the dynamic range of the signals reflected from the target 101.

Figure 2H:
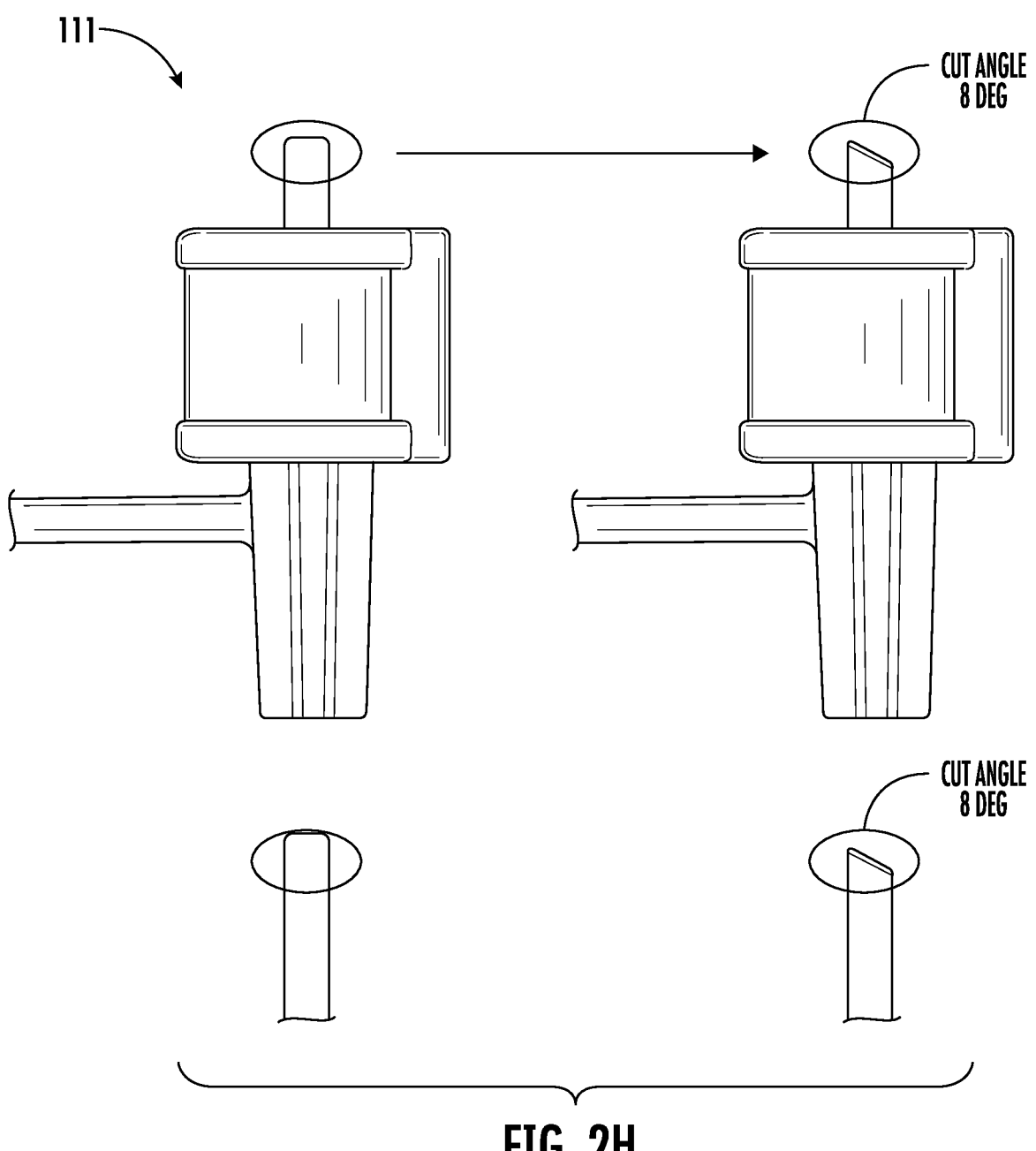
FIGS. 2H and 2I illustrate exemplary views of a proximal end of optical fiber, cut at specific angles, in accordance with some embodiments of the present disclosure.

In some embodiments of the aforementioned exemplary configurations, the proximal end 111 of the optical fiber can include a sub-miniature version A (SMA) connector, which may be polished or cut at an angle of 8 degrees, as shown in FIG. 2H. Cutting in a slant fashion at an 8 degree angle, as shown in this figure achieves diversion of the reflected light beams (unwanted reflections caused from the proximal end 111) from the proximal end 111 of the optical fiber 103, which in turn may reduce substantive noise and increase dynamic range. In some embodiments, the light signal (e.g., reflected light beam 223) that enters the light detector may contain one or more of: (a) reflections from port lens; (b) reflections from blast shield; (c) reflections from the proximal end 111 of the optical fiber; and/or (d) reflections from distal end 113 of the optical fiber.

Figure 2I:
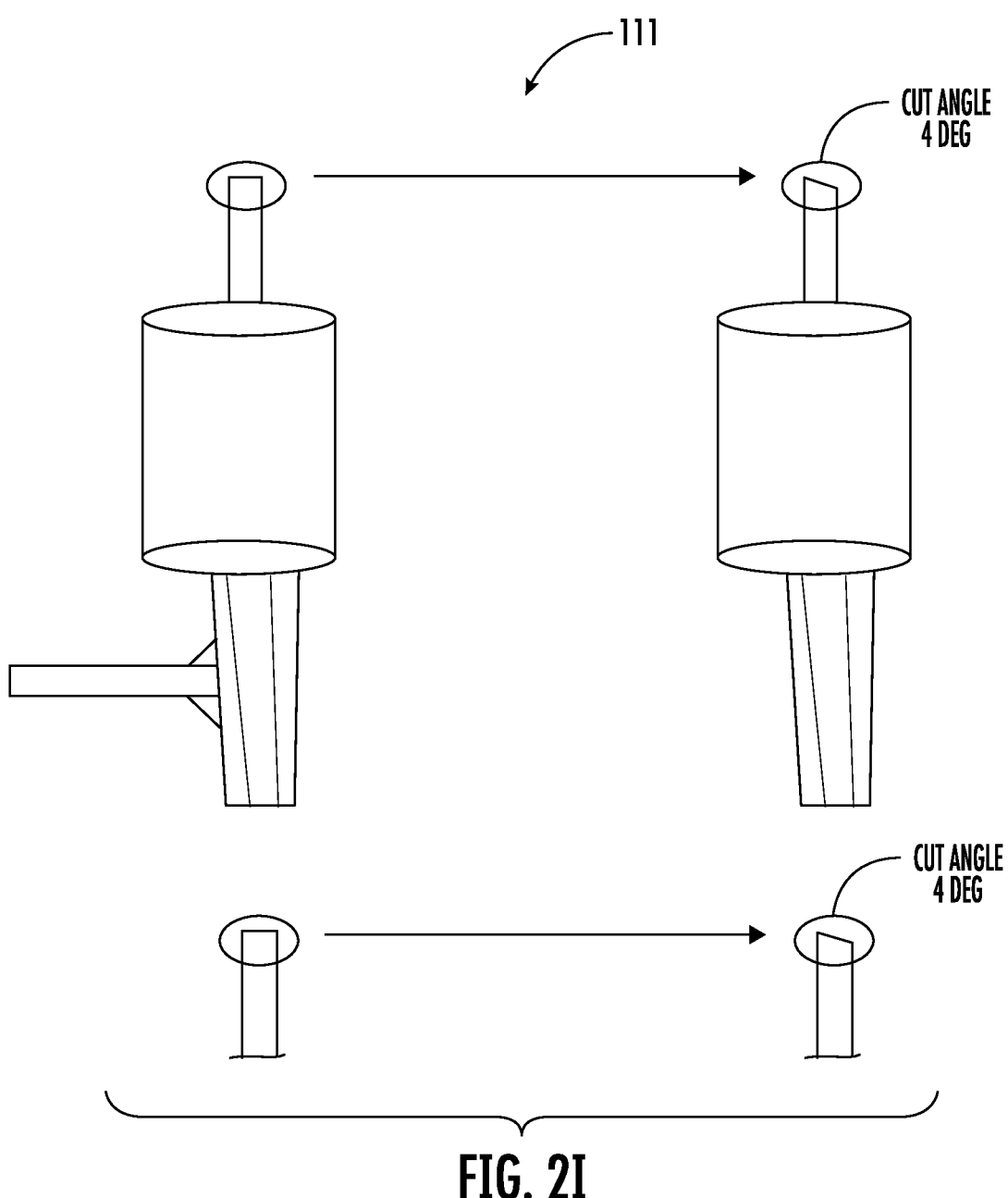

As explained above, AR coating at the proximal end of the optical fiber 103 may reduce reflections from the proximal end of the optical fiber 103 from 3.5% to approximately 0.5%. However, the angled finer proximal end of the optical fiber 103 helps in reducing unwanted reflections and improves the dynamic range of the signals reflected from the target 101. In some other embodiments, the SMA connector can be polished or cut at an angle of 4 degrees instead of 8 degrees, as shown in FIG. 2I. In various embodiments, cutting in a slant fashion at a 4-degree angle, such as instead of an 8-degree (or higher) angle, may improve signal robustness. In some embodiments, the smaller the cut angles of the SMA connector may result in more signal robustness of the optical fiber 103. In various embodiments, angles from approximately 2 degrees to approximately 8 degrees may be utilized. Generally, lower angles are harder to implement in optics. In other words, it is harder to snatch it from the main signal. However, light will not enter the fiber at higher angles (e.g., 10+ degrees).

FIG. 3A illustrates a flowchart showing a method 300 of estimating distance between a fiber end and a target in accordance with some embodiments of the present disclosure. The method 300 is described with reference to the architecture 100 and to the various configurations of the LETD 105 described above. It is to be appreciated however, that the method 300 could be implemented using an LETD different than that described herein. Embodiments are not limited in this context.

At block 301, the method 300 includes illuminating a target with laser light of a plurality of different wavelengths. For example, LETD 105 may utilize a plurality of laser light sources (e.g., 201a and 201b or 201a' and 201b') to illuminate target 101 with the laser light of the plurality of different wavelengths via the optical fiber 103. In some embodiments, the laser light of the plurality of different wavelengths may be provided to the optical fiber 103 for illuminating the target 101 using one of the configurations 200A-200G discussed above in the present disclosure. In various embodiments, the present disclosure may use light having two different wavelengths (e.g., light 225a and 225b or light 225a' and 225b') each wavelength having a different water absorption coefficient to ensure robustness with respect to different types of targets 101, target compositions, target colors, target surfaces, and the like.

In some embodiments, the two wavelengths may be selected such that, one is a wavelength with low water absorption coefficient (LO), and another is a wavelength with high water absorption coefficient (HI). As an example, the two wavelengths may be 1310 nm and 1340 nm. However, this example should not be construed as a limitation, as different wavelengths with different water absorption coefficients can be used. For example, 1260-1320 nm may be utilized for LO and 1330-1380 nm may be utilized for HI. More generally, any combination of pairs of wavelength water absorption coefficients with a 2:1 (or greater) ratio may be utilized. In some embodiments, one or more of the following pairs may be utilized for LO and HI lasers, respectively, 1310 nm and 1340 nm lasers, 1260 nm and 1340 nm lasers, 1260 nm and 1310 nm, and 1310 nm and 1550 nm lasers. As outlined above, in some embodiments, two laser sources (e.g., 201a and 201b or 201a' and 201b') can be used to emit light of two different wavelengths. In some embodiments, the laser light sources can be polarized laser sources, non-polarized laser sources, or a combination of polarized and non-polarized laser sources. As an example, to measure the distance between the distal end 113 of the optical fiber 103 and the target 101, a low-power infrared (IR) laser may be used, without limitation, to illuminate the target 101 via the optical fiber 103. In other embodiments, lasers other than IR lasers may be utilized. However, IR lasers may be utilized due to it not including visible light that may disturb users.

At block 303, the method 300 includes receiving reflected light beams from the target via an optical fiber. For example, the LETD system 105 may receive reflected light beams 223 from the target 101, via the optical fiber 103. In some embodiments, the reflected light beams 223 may include a mixture of reflections, such as from the proximal end 111 of the optical fiber 103, from the distal end 113 of the optical fiber 103, from the port 219, from the blast shield (not shown), and the like. In various embodiments, the LETD system 105 may be configured to identify the reflected light beams suitable for measuring intensity.

At block 305, the method includes measuring the intensity of the reflected light beams by detecting the reflected light beams using one or more light detectors and transmitting an indication (e.g., an electrical signal, or the like) of the intensity of the reflected light beam measured by the one or more light detectors to a processing unit. For example, the LETD system 105 may measure intensity of reflected light beams 223 (also referred to herein as returned signal) by detecting the returned signals 223 using the one or more light detectors provided in the LETD system 105. In some embodiments, since two different wavelengths are used for illuminating the target 101, the measured intensities are with respect to two different wavelengths. Therefore, the two measured intensities corresponding to the two different wavelengths of the laser sources (e.g., laser sources 201a and 201b or 201a' and 201b', or the like) may be transmitted to the processing unit 107 associated with the LETD system 105. In various embodiments, three or more different wavelengths may be utilized, measured, and/or transmitted.

At block 307, the method includes receiving, by the processing unit, the indication of the intensity of the reflected light beams 223 measured by the one or more light detectors. For example, processing unit 107 may receive electrical signals comprising indication(s) of the measured intensities of the returned signal 223 from the LETD system 105.

At block 309, the method includes estimating, by the processing unit, a distance between a distal end of the optical fiber and the target based on the intensity of the reflected light beams measured by the one or more light detectors. For example, processing unit 107 may estimate a distance between the distal end of the optical fiber 103 and the target 101 based on the measured intensities of the returned signal. In some embodiments, the processing unit 107 may substitute the measured intensities in the Equation 1 as shown below:

$$\text{Intensity of the returned signal} = R*e^{(-\lambda*X)} \qquad \text{Equation 1}$$

In the above Equation 1, "R" refers to target reflection coefficient, which is affected by target composition, target color/pigment, target angle, target surface and the like; "λ" refers to water absorption coefficient of a specific wavelength; and "X" refers to distance between the distal end of the optical fiber 103 and the target 101.

In the above Equation 1, "X" and "R" are unknown parameters which need to be determined by the processing unit 107. Therefore, in order to determine the values of "X" and "R", the processing unit 107 may substitute the two measured intensity values in the above Equation 1, thereby obtaining two equations with substituted values of measured intensity and the water absorption coefficient of the corresponding wavelength. For instance, the two equations with substituted values may be as shown below.

$$I_{(HI)} = R*e^{(-\lambda\_HI*X)} \qquad \text{Equation 1.1}$$

$$I_{(LO)} = R*e^{(-\lambda\_LO*X)} \qquad \text{Equation 1.2}$$

The processing unit 107 may further simplify the above substituted Equations 1.1 and 1.2 as shown in the below two steps:

Step 1: Compute ratio of measured intensity values obtained for the returned signal of two different wavelengths.

$$\frac{I_{(HI)}}{I_{(LO)}} = \frac{R}{R}*e^{(\lambda_{LO}-\lambda_{HI})*X} \qquad \text{Equation 2.1}$$

Step 2: Determine distance value using the natural logarithm as shown below:

$$X = \frac{\ln\left(\frac{I_{(HI)}}{I_{(LO)}}\right)}{\lambda_{LO}-\lambda_{HI}} \qquad \text{Equation 2.2}$$

Therefore, the processing unit 107 may estimate the distance (X) between the distal end 113 of the optical fiber 103 and the target 101, by simplifying Equations 1.1 and 1.2 as shown above. In the above Equation 2.2, "ln" refers to natural logarithm. In some embodiments, the distance (X) may be measured in millimeters. In some embodiments, "X" is the same distance for both wavelengths and R (target reflection) is almost identical for both wavelengths when the selected wavelengths are close to each other on the "nm scale". In some embodiments, wavelengths may be considered close to each other on the "nm scale" when they are within 250 nm (e.g., 1310 nm and 1340 nm or 1310 nm and 1550 m). However, in many embodiments, wavelengths with closer R values may be selected. Accordingly, 1310 nm and 1340 nm may be selected over 1310 nm and 1550 nm. With some examples of the present disclosure, the two laser sources (e.g., 201a and 201b or 201a' and 201b') can be arranged to emit light having wavelengths that are within 100 nm of each other.

The condition of the optical fiber 103 may be affected due to factors such as changes or degradation of the distal end 113 and/or proximal end 111 of the optical fiber 103, fiber bending effects on polarization scrambling, or any other degradations and changes occurring in the optical fiber 103. Changes in optical conditions of the optical fiber 103, specifically the tips/ends of the optical fiber 103, may adversely affect one or more of the quality of the irradiated beam, the intensity of the internal reflected light beams, the amount of back reflected light from a target which enters the fiber, the amount of energy that reaches a target, and the accuracy of measurements. This may affect the accuracy of the distance estimation, potentially leading to incorrect positioning of the optical fiber 103 during the treatment or miscalculating energy optimization which are based on distance estimation as described in U.S. Provisional Patent Application No. 63/118,117, which is incorporated herein by reference.

Internal reflections from planes associated with the fiber (e.g., the fiber proximal end or the fiber distal end) or planes associated with other optical elements which are optically connected with the fiber (e.g., lenses or shields) can generate parasitic and unwanted reflections. Moreover, these internal reflections may change over time due to fiber or other elements degradation. Also, fiber degradation may change the quality of the laser beam irradiated toward the target and/or the intensity of back reflected light from a target tissue, such as the reflected light that enters and passes through the optical fiber as beams 223a and 223b).

As such, with some embodiments, at block 309, method 300 can measure the initial internal reflections of each laser before a treatment starts to keep accurate distance measurements during fiber degradation and changes in internal reflections. In many such embodiments, the initial internal reflection values (or base values) may be recorded and utilized to monitor changes over time. For example, processing unit 107 can include circuitry (e.g., registers, memory, or the like) to store indications of the initial internal reflection values. In several embodiments, this process may be performed for one or more optical fibers 103 to be used with a laser system. For example, this process may be performed for each optical fiber 103 to be used with a laser system. Various embodiments described herein may monitor changes from the initial internal reflection values (e.g., stored in circuitry of processing unit 107, or the like) to dynamically calibrate distance measurements as provided herein.

In some embodiments, the processing unit 107 is configured to read (e.g., from a register, from memory, or the like) baseline values of such parasitic (e.g., unwanted) reflections using a system pre-treatment calibration process. In some embodiments, the system pre-treatment calibration process may include setting up a treatment fiber in water with no target. In this context, "no target" can be interpreted to mean that the closest target (e.g., a stone, a tumor, or the like) may be located far enough away from the tip of the fiber such that no light or substantially no light reflects off the target and into the optical fiber 103 as signal 223a. Such a distance may be, for example, 10 mm from the distal end 113 of the optical fiber 103, or more, for IR sources (e.g., 1310 nm and 1340 nm sources). However, if visual light (e.g., 400-700 nm) is utilized then a length greater than 10 mm may be utilized. Thereafter, under these conditions, the system may activate the lasers (e.g., 201a and 201b or 201a' and 201b') and measure the reflected signals 223 as described above. Since the reflected light 223a under these conditions (e.g., active laser in the presence of water but not target) is very low, the signals reaching the light detectors are related mainly to internal reflections associated with the optical fiber (e.g., from the port 219, the proximal end 111, the distal end 113, or the like).

The internal reflected (IR) light beams in such a scenario may be detected using the light detectors and the measured intensity values may be stored as $IR_{(HI)}$ and $IR_{(LO)}$, by the processing unit 107 (e.g., in a register, in memory circuitry, or the like). $IR_{(HI)}$ may be the intensity of the internal reflections of incident light having higher water absorption co-efficient when there is no target close to the fiber tip (e.g., the distal end 113) while $IR_{(LO)}$ may be the intensity of internal reflections of incident light having low water absorption co-efficient when there is no target close to the fiber tip (e.g., the distal end 113). Thereafter, during a therapy or treatment, when the laser is activated while the distal end 113 of the optical fiber is placed at a closer distance to the target 101, return signals 223a may be reflected backward through the optical fiber and detected using the light detectors described herein.

In addition to calculating the measured intensity values as described above, processing unit 107, at block 309, can store the measured intensity values (e.g., in a register, in memory circuitry, or the like) as $I_{(HI)}$ which may be an indication of the intensity of returned signal from a target 101 (e.g., tissue, stone, etc.) corresponding to wavelengths having higher water absorption co-efficient (HI) and store $I_{(LO)}$ which may be an indication of the intensity of returned signal from a target 101 (e.g., tissue, stone, etc.) corresponding to wavelengths having lower water absorption co-efficient (LO). However, to eliminate values of parasitic (or unwanted) reflections from readings of the actual returned signals 223, the processing unit 107 may subtract and/or reduce the $IR_{(HI)}$ from reading of the actual returned signal $I_{(HI)}$ as shown in the below Equation 3.1, and $IR_{(LO)}$ from reading of the actual returned signal $I_{(LO)}$ as shown in the below Equations 3.1 and 3.2, respectively.

$$I'_{(HI)}=I_{(HI)}-IR_{(HI)} \qquad\qquad \text{Equation 3.1}$$

$$I'_{(LO)}=I_{(LO)}-IR_{(LO)} \qquad\qquad \text{Equation 3.2}$$

In the above Equation 3.1, I'm refers to a new calculated intensity of returned signals corresponding to wavelengths having higher water absorption co-efficient (HI) (without the parasitic (or unwanted) reflections); $I_{(HI)}$ refers to a measured intensity of returned signal corresponding to wavelengths having higher water absorption co-efficient (HI) (with the parasitic (or unwanted reflections); and $IR_{(HI)}$ refers to a measured intensity of internal reflections of incident light having higher water absorption co-efficient (measured with "no target").

Similarly, in the above Equation 3.2, $I'_{(LO)}$ refers to a new calculated intensity of returned signals corresponding to wavelengths having lower water absorption co-efficient (LO) (without the parasitic (or unwanted) reflections); $I_{(LO)}$ refers to a measured intensity of returned signals corresponding to wavelengths having lower water absorption co-efficient (LO) (with the parasitic (or unwanted) reflections); and $IR_{(LO)}$ refers to measured intensity of internal reflections of incident light having lower water absorption co-efficient (measured with "no target").

Therefore, using the new intensity calculated values $I'_{(HI)}$ and $I'_{(LO)}$, the processing unit 107 may determine the distance between the distal end 113 of the optical fiber 103 and the target 101, by substituting the new "calibrated" values $I'_{(HI)}$ and $I'_{(LO)}$, in Equation 2.2 as shown below:

$$X = \frac{\ln\left(\frac{I_{(HI)} - IR_{(HI)}}{I_{(LO)} - IR_{(LO)}}\right)}{\lambda_{LO} - \lambda_{HI}}$$

In some embodiments, the above equation of "X" may also be indicated as shown below:

$$X = \frac{\ln\left(\frac{I'_{(HI)}}{I'_{(LO)}}\right)}{\lambda_{LO} - \lambda_{HI}}$$

As mentioned above, the internal reflections may not be constant over time and may change due to some changes in internal optical parameters of the system (as opposed to changes due to the dynamics of the treatment environment which is external to the system) such as the optical quality of the distal end 113 of the optical fiber 103. Due to one or more of the power level of the treatment beam 233, cavitation effects that take place at the distal end 113 (or tip) of the optical fiber 103, and the liquid environment in which the fiber is disposed during treatment, the optical fiber undergoes various amounts of degradation, primarily at the distal end 113 (or the tip). Accordingly, in several embodiments, "real-time" or "dynamic" calibration may be performed by monitoring the reflected signals 223 repeatedly during a treatment and dynamically accounting for or adjusting for such changes in internal reflections. For example, for performing such real-time calibration, as shown in configurations 200D-200G, a calibration laser (e.g., laser source 201c or laser source 201c') can be utilized to facilitate more accurate distance estimation that accounts for such degradation of the optical fiber 103.

As explained with respect to configurations 200D-200G, the calibration laser beam (e.g., 225c or 225c') has a wavelength with a very high absorption co-efficient in water. As an example, the wavelength of the polarized laser source 201c, or non-polarized laser source 201c' may be 1435 nm. Since laser beams generated by the calibration laser 201c and 201c' are so strongly absorbed by the liquid environment, as explained above, hardly any back reflection 223a associated with these laser beams goes back into the fiber. Therefore, while the calibration laser source (e.g., 201c or 201c') is active, the reflected signals 223 having a wavelength of the calibration laser source 201c or 201c' mainly are associated with (or indicative of) internal reflections.

In several embodiments, processing unit 107, at block 309, can be configured to read and store one or more base values for the internal reflections of the architecture 100 associated with the laser source 201c or 201c' before a treatment starts. These one or more base values may represent the "quality" of the optical fiber 103 (e.g., the optical quality of the distal end 113) before the treatment starts and can be stored (e.g., in a register, in memory circuitry, or the like) by the processing unit 107. Further, processing unit 107 may be configured to continue measuring, in "real-time" during a treatment, internal reflections of light emitted by the calibration laser source 201c or 201c' to identify deviations from the base values. Monitoring these deviations provides an indication as to a degradation of the optical quality of the optical fiber and may be used to correct any measured back reflected intensity associated with signal 223a. In many embodiments, based on the readings of the internal reflections of light emitted by the calibration laser source 201c or 201c', processing unit 107 may rectify calibration parameters for the main laser sources 201a and 201b or 201a' and 201b'.

In some embodiments, method 300 can include a block for a calibration process. For example, processing unit 107 can read and store one or more internal reflections values associated with light emitted by the calibration laser 201c or 201c' where the system is activated in water. Since calibration laser 201c and 201c' is so highly absorbed in water, there may be much less sensitivity, relative to measurements of reflected signals associated with light emitted by lasers 201a and 201b or 201a' and 201b', to the distance to a target 101 during the calibration readings of 201c or 201c'. As will be explained in more detail below, this can provide the continuation of calibration laser measurements during treatment when a target may also be close to the tip of the fiber.

Thereafter, the target 101 can be illuminated using one of the exemplary configurations 200D-200G with lasers 201a and 201b or 201a' and 201b'. The reflected light beams 223a and 223b in such a scenario may be detected using the light detectors and the processing unit 107 can store the measured intensity values as $I_{(HI)}$, $I_{(LO)}$ together with additional and associated measurements of the internal reflections of calibration laser $IR_{(CAL)}$. $I_{(HI)}$ may be the intensity of the back reflections from the target of incident light having a higher water absorption co-efficient, $I_{(LO)}$ may be the intensity of the back reflections from the target of incident light having a low water absorption co-efficient, and $IR_{(CAL)}$ may be the intensity of the internal reflections of incident light from calibration laser 201c or 201c'.

In some embodiments, the presence or absence of a target 101 may not affect the reflections $IR_{(CAL)}$ because the incident light from the calibration laser source 201c or 201c' is highly absorbed by water. As a result, changes in the $IR_{(CAL)}$ value may be a result of changes in degradation of the optical fiber 103, specifically the tips (e.g., the distal end 113, or the like) of the optical fiber 103. In some embodiments, based on relative changes of the $IR_{(CAL)}$ value, the processing unit 107 may adjust the previously measured $IR_{(HI)}$ and $IR_{(LO)}$ values or the currently measured $I_{(LO)}$ or $I_{(HI)}$.

Thereafter, during a treatment (e.g., when the laser is activated to treat a target 101) when there is the presence of the target 101 (e.g., when the target 101 is at a distance close enough to generate back reflection signals 223a, such as when the target is in a distance less than or equal to 10 mm from the distal end 113 of the optical fiber 103), the back reflected light beams 223a for laser source 201a or 201a' and for laser source 201b or 201b' and the internal reflection 223c from the calibration laser source 201c or 201c' may be detected using the light detectors. The processing unit 107, at block 309, can store the measured intensity values as $I_{(HI)}$ which may be representative of the intensity of returned signals corresponding to light having wavelengths with a higher water absorption co-efficient (HI), $I_{(LO)}$ which may be representative of the intensity of returned signals corresponding to light having wavelengths with a lower water absorption co-efficient (LO), and $IR_{(CAL)}$ which may be representative of the intensity of returned internal reflection signals corresponding to light having wavelengths with a higher still water absorption co-efficient (e.g., light emitted by the calibration laser source 201c or 201c'. Further, to determine a calibration factor, the processing unit 107 may divide $IR_{(CAL-PRE)}$ from the calibration process pre-treatment from $IR_{(CAL-DUR)}$ from a calibration process done during a treatment as shown in the below Equation 4.

$$\text{Calibration Factor } (CF) = \frac{IR_{(CAL-PRE)}}{IR_{(CAL-DUR)}} \qquad \text{Equation 4}$$

When the internal reflections of calibration laser source 201c or 201c' before and during a treatment are the same and there are no changes in the optical fiber 103 the calibration factor may be "1". Further, to rectify parameters for the main lasers 201a and 201b or 201a' and 201b' based on the calibration factor, the processing unit 107 may use the calibration factor as shown in the below Equations 5.1 and 5.2.

$$I''_{(HI)} = I_{(HI)} - IR_{(HI)} \times CF \qquad \text{Equation 5.1}$$

$$I''_{(LO)} = I_{(LO)} - IR_{(LO)} \times CF \qquad \text{Equation 5.2}$$

In the above Equation 5.1, $I''_{(HI)}$ refers to a new calibrated intensity of back reflected signals from a target which is corresponding to light having wavelengths with a higher water absorption co-efficient (HI); $I_{(HI)}$ refers to the measured intensity of the back reflected signals from a target which is corresponding to light having wavelengths with the higher water absorption co-efficient (HI); $IR_{(HI)}$ refers to the measured intensity of the internal reflection of incident laser light having wavelengths with the higher water absorption co-efficient (measured with "no target"); and CF refers to calibration factor determined using Equation 4.

In the above Equation 5.2, $I''_{(LO)}$ refers to a new calibrated intensity of back reflected signals from a target which is corresponding to light having wavelengths with a lower water absorption co-efficient (LO); $I_{(LO)}$ refers to the measured intensity of back reflected signals from a target which is corresponding to light having wavelengths with the lower water absorption co-efficient (LO); $IR_{(LO)}$ refers to the measured intensity of internal reflection of incident laser light having wavelengths with the lower water absorption co-efficient (measured with "no target"); and CF refers to calibration factor determined using Equation 4.

Therefore, using the new calibrated intensity values $I''_{(HI)}$ and $I''_{(LO)}$, the processing unit 107 at block 309, can determine the distance between distal end 113 of the optical fiber 103 and the target 101, by substituting the new calibrated values $I''_{(HI)}$ and $I''_{(LO)}$, into Equation 2.2 as shown below:

$$X = \frac{\ln\left(\dfrac{I_{(HI)} - IR_{(HI)} * CF}{I_{(LO)} - IR_{(LO)} * CF}\right)}{\lambda_{LO} - \lambda_{HI}} \qquad \text{Equation 2.2}$$

Therefore, in this way, system pre-treatment calibration and real-time calibration may be performed and utilized to update the calibration factor (e.g., via processing unit 107) in real-time to dynamically account for changes (e.g., degradation, or the like) of the fiber during operation. In several embodiments the pre-treatment and real-time calibrations may be performed to ensure the accuracy of the estimated distance between the distal end 113 of the optical fiber 103 and the target 101 when the fiber undergoes degradation.

At block 311, the method includes indicating, by the processing unit 107, the distance estimated (e.g., at block 309) between the distal end 113 of the optical fiber 103 and the target 101 via an indicator. For example, the processing unit 107 cause the estimated distance between the distal end of the optical fiber 103 and the target 101 to be indicated via an indicator 109 associated with the processing unit 107. As a specific example, the indicator 109 may include one or more of a visual indicator, an audio indicator, and a haptic indicator. Accordingly, processing unit 107, at block 311, can send a control signal to the indicator 109 to cause the indicator to indicate (e.g., display, audibly signal, haptically signal, or the like) an indication of the estimated distance, In some embodiments, based on the estimated distance between the distal end of the optical fiber 103 and the target 101, one or more of the position of the optical fiber 103, the orientation of the optical fiber 103, characteristics of the treatment beam, and the like may be varied, in real-time, to affect the treatment beam accurately and efficiently on the target 101, such as through more accurate aiming.

FIG. 3B illustrates a flowchart showing a method 350 of estimating distance between a fiber end and a target in accordance with some embodiments of the present disclosure. The method 350 is described with reference to the architecture 100 and to the various configurations of the LETD 105 described above. It is to be appreciated however, that the method 300 could be implemented using an LETD different than that described herein. Embodiments are not limited in this context.

At block 351, the method 350 includes determining a first intensity value based on first reflected laser light corresponding to laser light of a first wavelength, wherein the laser light of the first wavelength exits a distal end 113 of an optical fiber 103, and the first reflected laser light is reflected by a target 101 and enters the distal end 113 of the optical fiber 103. For example, processing unit 107 may determine a first intensity value based on reflected laser light 223a corresponding to light having a wavelength with a high water absorption coefficient. In some embodiments, the laser light corresponding to the wavelength having a high water absorption coefficient may be generated by laser source 201a or 201a', as discussed above.

At block 353, the method 350 includes determining a second intensity value based on a second reflected laser light corresponding to laser light of a second wavelength, wherein the laser light of the second wavelength exits the distal end 113 of an optical fiber 103 and the second reflected laser light is reflected by the target 101 and enters the distal end 113 of the optical fiber. For example, processing unit 107, at block 350, may determine a second intensity value based on reflected laser light 223 corresponding to light having a wavelength with a low water absorption coefficient. In some embodiments, the laser light corresponding to the wavelength having a low water absorption coefficient may be generated by 201b or 201b', as discussed above.

At block 355, the method 350 includes computing a ratio of the first intensity value and the second intensity value. For example, processor 107, at block 355, may utilize Equation 2.1 to compute the ratio of the first intensity value and the second intensity value. At block 357, the method 350 includes estimating a distance between the distal end 113 of the optical fiber 103 and the target 101 based on the ratio of the first intensity value and the second intensity value derived at block 355. For example, processor 107, at block 357, may utilize Equation 2.2 to estimate the distance between the distal end 113 of the optical fiber 103 and the target 101 based on the ratio of the first intensity value and the second intensity value.

FIG. 3C illustrates a flowchart showing a method 380 of estimating distance between a fiber end and a target in accordance with some embodiments of the present disclosure. The method 380 is described with reference to the architecture 100 and to the various configurations of the LETD 105 described above. It is to be appreciated however, that the method 300 could be implemented using an LETD different than that described herein. Embodiments are not limited in this context.

At block 381, the method 380 includes illuminating a target with laser light of a plurality of different wavelengths. For example, one of the configurations 200A-200G may be utilized to illuminate target 101 with laser light 221 of a plurality of different wavelengths. In several embodiments, the laser light 221 of the plurality of different wavelengths can include one or more of light beams 225a, 225b, 225c, 231 and/or 233.

At block 383, the method 380 includes receiving reflected light beams from the target via an optical fiber. For example, one of the configurations 200A-200G may be utilized to receive reflected light beams 223 (e.g., corresponding to light reflected from the target 101) and back transmitted via optical fiber 103. In several embodiments, the reflected light beams 223 can be reflected off the target 101 and enter the distal end 113 of the optical fiber 103 and as such may include reflected light 223a. The reflected lights 223a can also include light reflected from optical components within the system (e.g., the proximal end 111, the distal end 113, or the like) and can include reflected light 223c which corresponds to reflected light associated with calibration light beam 225c.

At block 385, the method 380 includes measuring intensity of the reflected light beams 223 with one or more light detectors. In many embodiments, one of the configurations 200A-200G may be utilized to measure the intensity of the reflected light beams 223 with one or more light detectors. For example, first light detector 215 and second light detector 217 may be utilized to measure the intensity of the reflected light beams 223. In another example, third light detector 227 may be utilized to measure the intensity of the reflected light beams 223.

At block 387, the method 380 includes estimating a distance between a distal end 113 of the optical fiber 103 and the target 101 based on intensity of the reflected light beams 223 measured with the one or more light detectors. For example, processing unit 107 may be utilized to estimate the distance between a distal end 113 of the optical fiber 103 and the target 101 based on intensity of the reflected light beams 223 measured with the one or more light detectors. In some embodiments, processing unit 107 may be comprised in one or more portions of computer system 400.

Figure 4:
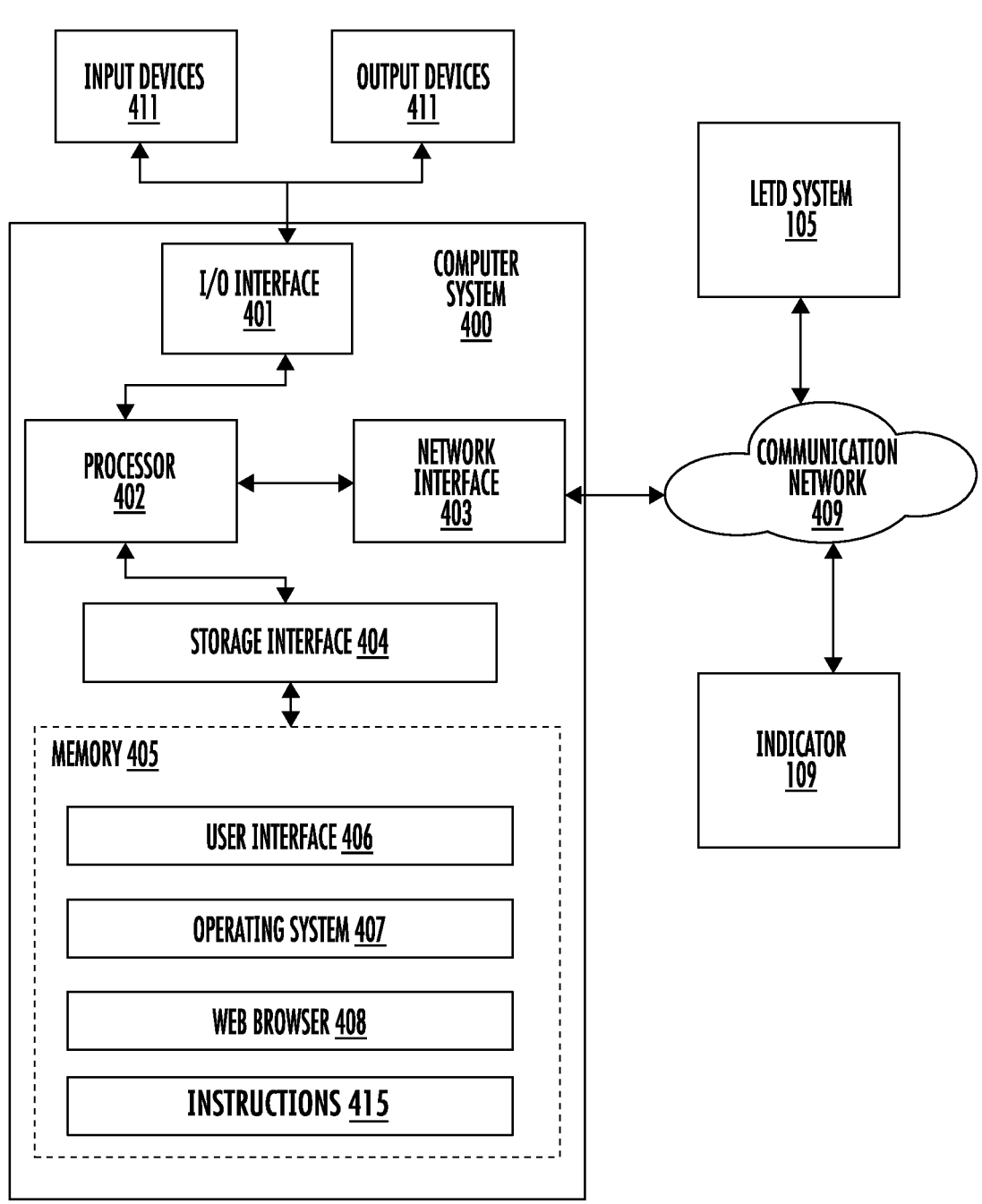
FIG. 4 illustrates a block diagram of an exemplary computer system for implementing embodiments consistent with the present disclosure.

FIG. 4 is a block diagram of an exemplary computer system 400 for implementing embodiments consistent with the present disclosure. The computer system 400, or one or more portions thereof, may comprise processing unit 107. Said differently, processing unit 107 can be implemented by computer system 400. In some such embodiments, the computer system 400 may be utilized to estimate the distance between a distal end 113 of an optical fiber 103 and a target 101. Embodiments are not limited in this context.

The computer system 400 may include a central processing unit ("CPU" or "processor") 402. The processor 402 may include at least one data processor arranged to execute instructions or program components to carry out the operations described above (e.g., with respect to methods 300, 350, and/or 380). A user may include a person, a person using a device such as those included in this disclosure (e.g., a physician, a nurse, a technician, or the like), or the device itself. The processor 402 may include specialized processing units such as integrated system (bus) controllers, memory management control units, floating point units, graphics processing units, digital signal processing units, application specific integrated circuits (ASICS), field programmable gate arrays (FPGAs), or commercial processing units. The processor 402 may be configured for and arranged in communication with input devices 411 and/or output devices 412 (e.g., via I/O interface 401, or the like). The I/O interface 401 may employ communication protocols or methods such as, without limitation, audio, analog, digital, stereo, IEEE-1394, serial bus, Universal Serial Bus (US B), infrared, PS/2, BNC, coaxial, component, composite, Digital Visual Interface (DVI), high-definition multimedia interface (HDMI), Radio Frequency (RF) antennas, S-Video, Video Graphics Array (VGA), IEEE 802.xx/b/g/n/x, Bluetooth, cellular (e.g., Code-Division Multiple Access (CDMA), High-Speed Packet Access (HSPA+), Global System For Mobile Communications (GSM), Long-Term Evolution (LTE), WiMax, or the like), etc.

Using the I/O interface 401, computer system 400 may communicate with input devices 411 and/or output devices 412. In some embodiments, the processor 402 may be configured for and arranged in communication with a communication network 409, (e.g., via a network interface 403, or the like). The network interface 403 may be utilized to communicate via the communication network 409. The network interface 403 may employ connection protocols including, without limitation, direct connect, Ethernet (e.g., twisted pair 10/100/1000 Base T), Transmission Control Protocol/Internet Protocol (TCP/IP), token ring, IEEE 802.11a/b/g/n/x, etc. Using the network interface 403 and the communication network 409, the computer system 400 may communicate with an LETD system 105 and/or an indicator 109. In some embodiments, one or more portions of the computer system 400 may be integrated into the LETD system 105. In some such embodiments, one or more components of the LETD system 105 (e.g., power detectors and/or light detectors) may comprise an input device 411.

The communication network 409 can be implemented as one of the different types of networks, such as intranet or Local Area Network (LAN), Closed Area Network (CAN) and such. The communication network 409 may either be a dedicated network or a shared network, which represents an association of the different types of networks that use a variety of protocols, for example, Hypertext Transfer Protocol (HTTP), CAN Protocol, Transmission Control Protocol/Internet Protocol (TCP/IP), Wireless Application Protocol (WAP), etc., to communicate with each other. Further, the communication network 409 may include a variety of network devices, including routers, bridges, servers, computing devices, storage devices, etc. In some embodiments, the processor 402 may be disposed in communication with a memory 405 (e.g., RAM, ROM, etc. not shown in FIG. 4) via a storage interface 404. The storage interface 404 may connect to memory 405 including, without limitation, memory drives, removable disc drives, etc., employing connection protocols such as Serial Advanced Technology Attachment (SATA), Integrated Drive Electronics (IDE), IEEE-1394, Universal Serial Bus (USB), fiber channel, Small Computer Systems Interface (SCSI), etc. The memory drives may further include a drum, magnetic disc drive, magneto-optical drive, optical drive, Redundant Array of Independent Discs (RAID), solid-state memory devices, solid-state drives, etc.

The memory 405 may store a collection of program or database components, including, without limitation, a user interface 406, an operating system 407, a web browser 408, and instructions 415, etcetera. In various embodiments, instructions 415 may include instructions that when executed by the processor 402 cause the processor 402 to perform one or more techniques, steps, procedures, and/or methods described hereby, such as to estimate a distance or perform a calibration. For example, instructions to perform method 300, 350, and/or 380 may be stored in memory 405. In many embodiments, memory 405 includes at least one non-transitory computer-readable medium. For example memory 405 can be a memory device comprising memory circuitry arranged to non-transitorily store instructions 415. In some embodiments, the computer system 400 may store user/application data, such as the data, variables, records, etc. as described in this disclosure. Such databases may be implemented as fault-tolerant, relational, scalable, secure databases such as Oracle or Sybase.

The operating system 407 may facilitate resource management and operation of the computer system 400. Examples of operating systems include, without limitation, APPLE® MACINTOSH® OS X®, UNIX®, UNIX-like system distributions (E.G., BERKELEY SOFTWARE DISTRIBUTION® (BSD), FREEBSD®, NETBSD®, OPENBSD, etc.), LINUX® DISTRIBUTIONS (E.G., RED HAT®, UBUNTU®, KUBUNTU®, etc.), IBM® OS/2®, MICROSOFT® WINDOWS® (XP®, VISTA®/7/8, 10 etc.), APPLE® IOS®, GOOGLE™ ANDROID™, BLACKBERRY® OS, or the like. The User interface 406 may facilitate display, execution, interaction, manipulation, or operation of program components through textual or graphical facilities. For example, user interfaces may provide computer interaction interface elements on a display system operatively connected to the computer system 400, such as cursors, icons, checkboxes, menus, scrollers, windows, widgets, etc. Graphical User Interfaces (GUIs) may be employed, including, without limitation, Apple® Macintosh® operating systems' Aqua®, IBM® OS/2®, Microsoft® Windows® (e.g., Aero, Metro, etc.), web interface libraries (e.g., ActiveX®, Java®, JavaScript®, AJAX, HTML, Adobe® Flash®, etc.), or the like.

In some embodiments, the computer system 400 may implement the web browser 408 stored program components. The web browser 408 may be a hypertext viewing application, such as MICROSOFT® INTERNET EXPLORER®, GOOGLE™ CHROME™, MOZILLA® FIREFOX®, APPLE® SAFARI®, etc. Secure web browsing may be provided using Secure Hypertext Transport Protocol (HTTPS), Secure Sockets Layer (SSL), Transport Layer Security (TLS), etc. Web browsers 408 may utilize facilities such as AJAX, DHTML, ADOBE® FLASH®, JAVASCRIPT®, JAVA®, Application Programming Interfaces (APIs), etc. In some embodiments, the computer system 400 may implement a mail server stored program component. The mail server may be an Internet mail server such as Microsoft Exchange, or the like. The mail server may utilize facilities such as Active Server Pages (ASP), ACTIVEX®, ANSI® C++/C#, MICROSOFT® .NET, CGI SCRIPTS, JAVA®, JAVASCRIPT®, PERL®, PHP, PYTHON®, WEBOBJECTS®, etc. The mail server may utilize communication protocols such as Internet Message Access Protocol (IMAP), Messaging Application Programming Interface (MAPI), MICROSOFT® exchange, Post Office Protocol (POP), Simple Mail Transfer Protocol (SMTP), or the like. In some embodiments, the computer system 400 may implement a mail client stored program component. The mail client may be a mail viewing application, such as APPLE® MAIL, MICROSOFT® ENTOURAGE®, MICROSOFT® OUTLOOK®, MOZILLA® THUNDERBIRD®, etc.

Furthermore, one or more computer-readable storage media may be utilized in implementing embodiments consistent with the present disclosure. A computer-readable storage medium refers to any type of physical memory on which information or data readable by a processor may be stored. Thus, a computer-readable storage medium may store instructions for execution by one or more processors, including instructions for causing the processor(s) to perform steps or stages consistent with the embodiments described herein. The term "computer-readable medium" should be understood to include tangible items and exclude carrier waves and transient signals, i.e., non-transitory. Examples include Random Access Memory (RAM), Read-Only Memory (ROM), volatile memory, non-volatile memory, hard drives, Compact Disc (CD) ROMs, Digital Video Disc (DVDs), flash drives, disks, and any other known physical storage media.

In various embodiments, the present disclosure may provide a variety of technical effects and improvements. For example, the present disclosure may enable estimation of distance between a distal end of an optical fiber and a target, by using laser light of two different wavelengths (e.g., one having a low water absorption coefficient and the other having a high water absorption coefficient). Estimation of the distance based on such wavelength selection, can provide robustness with respect to different types of targets, target compositions, target colors, target surfaces and the like. The wavelength modulation-based techniques and systems disclosed in the present disclosure can be provided to estimate a distance between the distal end of an optical fiber and a target and can facilitate an accurate estimation of the distance. Further, the present disclosure provides processes of estimation of a distance between a distal end of an optical fiber and a target for various types of targets, and can provide for estimation of the distance for more and more varied target than conventionally possible. Accordingly, the present disclosure provides systems and methods to more accurately aiming at a target than conventionally possible. More accurate aiming can eliminate or reduce ablating and/or fragmenting incorrect portions of the target, which itself could lead to adverse outcomes and/or permanent damages. Also, more accurate aiming consumes less time in ablating and/or fragmenting the target.

In several embodiments, the present disclosure may be used to accurately position and/or aim a treatment beam, such as in low-visibility environments (e.g., environments including dust or target debris). For example, during treatment of a target (e.g., kidney stones) water may get turbid due to the presence of stone fragments or dust. This may reduce (or prevent) the ability to see the target (e.g., the kidney stone). In such scenarios, the present disclosure provides a system to accurately recognize and inform the treating physician about placement of the optical fiber (e.g., whether the fiber is placed in front of the target or whether there is no target detected Further, in many embodiments, the present disclosure may be used for distance measurement. For example, the target (e.g., kidney stone) may move around during treatment, which may lead to laser light associated with a treatment beam being incident on unwanted areas (e.g., healthy tissue, or the like) as opposed to being incident on the target. Therefore, the present disclosure may enable automatic and real-time monitoring of the distance between the optical fiber and the target, which in turn can reduce, or eliminate, the possibility of lasing unwanted areas.

Still further, in various embodiments, the present disclosure may be used for the purpose of controlling and/or adjusting one or more operational parameters. For example, during the treatment, the target may move back and forth, or may change its shape and size. Therefore, parameters pre-set for the laser sources before initiating lasing on the target, may become less effective. Conventionally, such pre-set parameters are manually changed which may be error prone and time consuming, or in some cases the pre-set parameters may be left unchanged which may lead to scenarios where the optical fiber may be too close or too far from the target. Therefore, the automatic and real-time monitoring of the distance between the optical fiber and the target, as disclosed in the present disclosure, can enable automatically changing the lasing pre-set parameters to adjust the lasing in accordance with the target shape, position, etcetera for best results.

With respect to the use of substantially any plural and/or singular terms herein, those having skill in the art can translate from the plural to the singular and/or from the singular to the plural as is appropriate to the context and/or application. The various singular and/or plural permutations are expressly set forth herein for sake of clarity and not limitation.

It will be understood by those within the art that, in general, terms used herein, and are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended. For example, as an aid to understanding, the detail description may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to disclosures containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations).

All of the devices and/or methods disclosed and claimed herein can be made and executed without undue experimentation in light of the present disclosure. While the devices and methods of this disclosure have been described in terms of preferred embodiments, it may be apparent to those of skill in the art that variations can be applied to the devices and/or methods and in the steps or in the sequence of steps of the method described herein without departing from the concept, spirit, and scope of the disclosure. All such similar substitutes and modifications apparent to those skilled in the art are deemed to be within the spirit, scope and concept of the disclosure as defined by the appended claims.

What is claimed is:

1. A system, comprising:
   a first laser source to generate laser light of a first wavelength;
   a second laser source to generate laser light of a second wavelength different from the first wavelength;
   an optical fiber having a distal end, the optical fiber configured to pass laser light from the first and second laser sources out of the distal end and to receive reflected laser light into the distal end;
   a light detector to measure intensity of the reflected light; and
   a processor and memory comprising instructions that when executed by the processor cause the processor to:

receive an indication of a first intensity value of the reflected light corresponding to the laser light of the first wavelength,
   receive an indication of a second intensity value of the reflected light corresponding to the laser light of the second wavelength,
   derive an adjusted first intensity value based on subtracting a first internal reflection values from the first intensity value,
   derive an adjusted second intensity value based on subtracting a second internal reflection values from the second intensity value, and
   estimate a distance between the distal end of the optical fiber and a target based on a ratio of the adjusted first intensity value of the reflected light and the adjusted second intensity value of the reflected light,
   wherein the first wavelength has a first water absorption coefficient higher than a second water absorption coefficient of the second wavelength.

2. The system of claim 1, wherein the ratio of the first water absorption coefficient to the second water absorption coefficient is at least 2 to 1.

3. The system of claim 2, wherein the first wavelength is approximately 1330 nm to approximately 1380 nm and the second wavelength is approximately 1260 nm to approximately 1320 nm.

4. The system of claim 3, comprising a third laser source to generate laser light of a third wavelength utilized to characterize a condition of the optical fiber, wherein the third wavelength has a third water absorption coefficient higher than the first and the second water absorption coefficients.

5. The system of claim 4, wherein the third wavelength comprises approximately 1435 nm, approximately 2100 nm, or a wavelength between approximately 1870 nm and approximately 2050 nm.

6. The system of claim 1, wherein one or more of the first and second laser sources comprise a polarization maintaining pigtailed fiber laser, a single mode pigtailed fiber laser, or a free space laser.

7. The system of claim 1, comprising a wave division multiplexer (WDM) coupled to a proximal end of the optical fiber, the WDM to arrange the laser light of the first wavelength and the laser light of the second wavelength to enter a proximal end of the optical fiber at one or more of a same point and a same angle.

8. At least one non-transitory computer-readable medium comprising a set of instructions that, in response to being executed by a processor circuit, cause the processor circuit to:
   determine a first intensity value based on first reflected laser light corresponding to laser light of a first wavelength, wherein the laser light of the first wavelength exits a distal end of an optical fiber and the first reflected laser light is reflected by a target and enters the distal end of the optical fiber;
   determine a second intensity value based on second reflected laser light corresponding to laser light of a second wavelength different from the first wavelength, wherein the laser light of the second wavelength exits the distal end of the optical fiber and the second reflected laser light is reflected by the target and enters the distal end of the optical fiber;
   derive an adjusted first intensity value based on subtracting a first internal reflection values from the first intensity value, derive an adjusted second intensity value based on subtracting a second internal reflection values from the second intensity value, and compute a ratio of the adjusted first intensity value and the adjusted second intensity value; and estimate a distance between the distal end of the optical fiber and the target based on the ratio of the adjusted first intensity value and the adjusted second intensity value, wherein the first wavelength has a first water absorption coefficient higher than a second water absorption coefficient of the second wavelength.

9. The at least one non-transitory computer-readable medium of claim 8, wherein the set of instructions, in response to execution by the processor circuit, further cause the processor circuit to determine an internal reflection value based on third reflected laser light corresponding to laser light of a third wavelength, wherein the laser light of the third wavelength exits a laser source and the at least a portion of the third reflected laser light is reflected by a distal end of the optical fiber.

10. The at least one non-transitory computer-readable medium of claim 9, wherein the set of instructions, in response to execution by the processor circuit, further cause the processor circuit to:

compare the internal reflection value to a baseline internal reflection value; and adjust an operating parameter of a treatment beam based on comparison of the internal reflection value to the baseline internal reflection value.

11. The at least one non-transitory computer-readable medium of claim 10, wherein the set of instructions, in response to execution by the processor circuit, further cause the processor circuit to:

compare the internal reflection value to a baseline internal reflection value;

characterize a condition of the optical fiber based on comparison of the internal reflection value to the baseline internal reflection value; and communicate an indication of the condition of the optical fiber via a user interface.

12. The at least one non-transitory computer-readable medium of claim 8, wherein the set of instructions, in response to execution by the processor circuit, further cause the processor circuit to communicate an indication of the distance estimated between the distal end of the optical fiber and the target via a user interface.

13. A method, comprising:

illuminating a target with laser light of a plurality of different wavelengths;

receiving reflected light beams from the target via an optical fiber;

measuring intensity of the reflected light beams with one or more light detectors, comprising at least:

measuring a first intensity value of the reflected light beams corresponding to laser light of a first wavelength, and measuring a second intensity value of the reflected light beams corresponding to laser light of a second wavelength different from the first wavelength;

deriving an adjusted first intensity value based on subtracting a first internal reflection values from the first intensity value;

deriving an adjusted second intensity value based on subtracting a second internal reflection values from the second intensity value;

computing a ratio of the adjusted first intensity value and the adjusted second intensity value; and estimating a distance between a distal end of the optical fiber and the target based on the ratio, wherein the first wavelength has a first water absorption coefficient higher than a second water absorption coefficient of the second wavelength.

14. The method of claim 13, comprising emitting the laser light of the plurality of different wavelengths via the optical fiber to illuminate the target.

* * * * *